US010710957B2

(12) United States Patent
Phanstiel, IV et al.

(10) Patent No.: US 10,710,957 B2
(45) Date of Patent: Jul. 14, 2020

(54) MOTUPORAMINE DERIVATIVES AS ANTIMICROBIAL AGENTS AND ANTIBIOTIC ENHANCERS AGAINST RESISTANT GRAM-NEGATIVE BACTERIA

(71) Applicants: University of Central Florida Research Foundation, Inc., Orlando, FL (US); INSERM TRANSFERT, Paris (FR)

(72) Inventors: Otto Phanstiel, IV, Oviedo, FL (US); Jean-Michel Brunel, Marseilles (FR)

(73) Assignees: University of Central Florida Research Foundation, Inc., Orlando, FL (US); Inserm Transfert, S.A., Paris (FR)

( * ) Notice: Subject to any disclaimer, the term of this patent is extended or adjusted under 35 U.S.C. 154(b) by 0 days.

(21) Appl. No.: 15/866,081

(22) Filed: Jan. 9, 2018

(65) Prior Publication Data
US 2018/0258029 A1 Sep. 13, 2018

Related U.S. Application Data

(60) Provisional application No. 62/444,050, filed on Jan. 9, 2017.

(51) Int. Cl.
| | |
|---|---|
| C07C 211/17 | (2006.01) |
| A61K 45/06 | (2006.01) |
| A61K 31/132 | (2006.01) |
| A61P 31/04 | (2006.01) |
| A61K 31/7048 | (2006.01) |
| A61K 31/165 | (2006.01) |
| A61K 31/32 | (2006.01) |
| C07D 225/02 | (2006.01) |
| A61K 31/546 | (2006.01) |
| A61K 31/65 | (2006.01) |
| A61K 31/16 | (2006.01) |

(52) U.S. Cl.
CPC .......... *C07C 211/17* (2013.01); *A61K 31/132* (2013.01); *A61K 31/16* (2013.01); *A61K 31/165* (2013.01); *A61K 31/32* (2013.01); *A61K 31/546* (2013.01); *A61K 31/65* (2013.01); *A61K 31/7048* (2013.01); *A61K 45/06* (2013.01); *A61P 31/04* (2018.01); *C07D 225/02* (2013.01); *C07C 2601/18* (2017.05); *Y02A 50/483* (2018.01)

(58) Field of Classification Search
None
See application file for complete search history.

(56) References Cited

U.S. PATENT DOCUMENTS

| 4,559,157 A | 12/1985 | Smith et al. |
|---|---|---|
| 4,608,392 A | 8/1986 | Jacquet et al. |
| 4,820,508 A | 4/1989 | Wortzman |
| 4,910,190 A | 3/1990 | Bergeson et al. |
| 4,938,949 A | 7/1990 | Borch et al. |
| 4,992,478 A | 2/1991 | Geria |
| 7,001,925 B1 | 2/2006 | Phanstiel |
| 7,728,040 B1 | 6/2010 | Phanstiel |
| 7,728,041 B2 | 6/2010 | Phanstiel |
| 7,910,363 B1 | 3/2011 | Phanstiel et al. |
| 8,497,398 B1 | 7/2013 | Phanstiel et al. |
| 9,150,495 B2 | 10/2015 | Phanstiel |
| 9,212,131 B2 | 12/2015 | Phanstiel et al. |
| 9,346,741 B2 | 5/2016 | Phanstiel et al. |
| 2006/0148904 A1* | 7/2006 | Protopopova .......... A61K 31/13 514/649 |
| 2015/0057361 A1* | 2/2015 | Phanstiel, IV ........ C07C 211/36 514/659 |

OTHER PUBLICATIONS

Bellevue et al. Bioorganic & Medicinal Chemistry Letters (1996), 2765-2770.*
Alhanout K., et al, "New insights into the antibacterial mechanism of action of squalamine", J. Antimicrob. Chemother., vol. 65, pp. 1688-1693 (2010).
Amaral L., et al, "Efflux pumps of Gram-negative bacteria: what they do, how they do it, with what and how to deal with them", J. Molnar, Front. Pharmacol., vol. 4, Issue 168, pp. 1-11 (2013).
Antoniadou A, et al., "Colistin-resistant isolates of Klebsiella pneumoniae emerging in intensive care unit patients: first report of a multiclonal cluster", Antimicrob. Chemother., vol. 59, pp. 786-790 (2007).
Askoura, M., et al., Efflux pump inhibitors (EPIs) as new antimicrobial agents against Pseudomonas aeruginosa, "Libyan J. Med.", vol. 6 (2011).
Yu Y., et al, "Simple Strategy for taming membrane-disrupting antibiotics", Bioconjugate Chem., vol. 27, pp. 2850-2853 (2016).
Biswas S., et al, Colistin: an update on the antibiotic of the 21st century, Expert Rev. Anti Infect. Ther. vol. 8, Issue 10, pp. 1-17 (2012).
Blanchet M., et al., "Polyamine derivatives: a revival of an old neglected scaffold to fight resistant Gram-negative bacteria", Future Med. Chem. 2016, 8, 963-973.
Bohnert J., et al al, "Determination of real-time efflux phenotypes in *Escherichia coli* AcrB binding pocket phenylalanine mutants using a 1,2'-dinaphthylamine Efflux Assay", PLoS One, vol. 6, pp. 1-5 (2011).
Brunel J, et al., "Polyamino generic derivatives as new chemosensitizers to combat antibiotic resistant Gram-negative bacteria", Bioorg. Med. Chem., vol. 21, pp. 1174-1179 (2013).
Buchwald H, et al., "Long-term, continuous intravenous heparin administration by an implantable infusion pump in ambnulatory patients with recurrent venous thrombosis", Surgery, vol. 88, pp. 507-516 (1980).
Coelho J., et al., "Occurrence of Carbapenem-resistant acinetobacter baumannii clones at multiple hospitals in london and southeast england", J. Clin. Microbiol., 2006, vol. 44, pp. 3623-3627.

(Continued)

*Primary Examiner* — Ana Z Muresan
(74) *Attorney, Agent, or Firm* — Timothy H. Van Dyke; Beusse, Wolter, Sanks & Maire PLLC

(57) ABSTRACT

Motuporamine agents having antimicrobial activity and uses thereof.

4 Claims, 12 Drawing Sheets

(56) References Cited

OTHER PUBLICATIONS

Djouhri-Bouktab L, et al, "Mini-review: polyamines metabolism, toxicity and potent therapeutical use", Anti-infective Agents 2014, vol. 12, pp. 95-103.
During M, et al., "Controlled release of dopamine from a polymeric brain implant: in vivo characterization", Ann. Neurol., vol. 25, pp. 351-356 (1989).
Falagas M, & Kasiakou S., "Colistin: the revival of polymyxins for the management of multidrug-resistant gram-negative bacterial infections", Clin. Infect. Dis. 2005, vol. 40, pp. 1333-1341.
Goodson, "Dental Applications", Medical Appl. of Controlled Release, vol. 2, pp. 115-138 (1984).
Hancock R., "The bacterial outer membrane as a drug barrier", Trends Microbiol. 1997, vol. 5, pp. 37-42.
Handzlik, J., et al., "Recent advances in multi-drug resistance (MDR) efflux pump inhibitors of gram-positive bacteria S aureus", antibiotics, pp. 28-25, vol. 2 (2013).
Howard III, M., et al., "Intracerebral drug delivery in rats with lesion-induced memory deficits", J. Neurosurg., vol. 71, pp. 105-112 (1989).
Jennings M, et al, "Quaternary ammonium compounds: an antimicrobial mainstay and platform for innovation to address bacterial resistance" , ACS Infect. Dis., 2015, pp. 288-303.
Kaur N, et al, "Synthesis and biological evaluation of dihydromotuporamine derivatives in cells containing active polyamine transporters", J. Med. Chem. 2005, vol. 48, pp. 3832-3839.
Labischinski H, et al, "High state of order of isolated bacterial lipopolysaccharide and its possible contribution to the permeation barrier property of the outer membrane", J Bacteriol. 1985, vol. 162, pp. 9-20.
Langer R., "New Methods of Drug Delivery", Science, vol. 249, pp. 1527-1533 (1990).
Langer R., et al, "Chemical and physical structure of polymers as carriers for controlled release of bioactive agents: a review", J. Macromolecular Science, vol. 23, pp. 61-126 (1983).
Levy R, et al., "Inhibition of calcification of bioprosthetic heart valves by local controlled-release diphosphonate", Science, vol. 228, pp. 190-192 (1985).
Lomovskaya O., et al., "Identification and characterization of inhibitors of multidrug resistance efflux pumps in pseudomonas aeruginosa: a novel agents for combination therapy", Antimicrob. Agents Chemother. 2001, vol. 45, pp. 105-116.
Lopez-Berestein G., et al, "Treatment of systemic fungal infections with liposomal amphotericin B", Arch Intern Med, vol. 149, pp. 317-327 (1989).
Mahamound, A., et al., "Antibiotic efflux pumps in gram-negative bacteria: the inhibitor response strategy", J. antimicrobial chemotherapy, pp. 1223-1229, vol. 59 (2007).
Mallea M., et al, "Porin alteration and active efflux: two in vivo drug resistance strategies used by Enterobacter aerogenes", Microbiology 1998, vol. 144, pp. 3003-3009.
Mariscal A, et al, "Fluorescent assay based on resazurin for detection of activity of disinfectants against bacterial biofilm", Appl. Microbiol. Biotechnol. 2009, vol. 82, pp. 773-783.
Matsumoto Y, et al, "Evaluation of multidrug efflux pump inhibitors by a new method using microfluidic channels", PLoS One 2011, vol. 6, pp. 1-12.
Members of the SFM Antibiogram Committee, "Comite de l'Antibiogramme de la Societe francaise de microbiologie report 2003", Int. J. Antimicrob. Agents 2003, vol. 21, pp. 364-391.
Mentzelopoulos, et al., "Prolonged use of carbapenems and colistin predisposes to ventilator-associated pneumonia by pandrug-resistant pseudomonas aeruginosa", Intensive Care Med. 2007, 33, 1524-1532.
Murata T., et al, "PhoPQ-Medicated regulation produces a more robust permeability barrier in the outer membrane of Salmonella enterica serovar typhimurium", J. Bacteriol. 2007, vol. 189, pp. 7213-7222.
Muth A, et al, "Polyamine transport inhibitors: design, synthesis, and combination therapies with difluoromethylornithine", J. Med. Chem. 2014, vol. 57, pp. 348-363.
Muth A, et al, "Synthesis and biological evaluarion of antimetastatic agents predicated upon dihydromotuporamine C and its carbocyclic derivatives", J. Med. Chem. 2014, vol. 57, pp. 4023-4034.
Nikaido H., "Molecular basis of bacterial outer membrane permeability revisited", Microbiol. Mol. Biol. Rev. 2003, vol. 67, pp. 593-656.
Nikaido, "*Escherichia coli* and *Salmonella*: cellular and molecular biology", American Society for Microbiology, vol. 2, 1996, 29-47.
Opperman T.,& Nguyen S., "Recent advances toward a molecular mechanism of efflux pump inhibition", Fronteirs in microbiology, pp. 1-16, vol. 6 (2015).
Peppas N, "Mathematical modeling of diffusion processes in drug delivery polymeric systems", Controlled Drug Bioavailability, pp. 203-237 (1984).
Phanstiel IV, et al, "Structure-activity investigations of polyamine-anthracene conjugates and their uptake via the polyamine transporter", Amino Acids 2007, vol. 33, pp. 305-313.
Pieri C, et al, "New Ianthelliformisamine derivatives as antibiotic enhancers against resistant gram-negative bacteria", J. Med. Chem. 2014, vol. 57, pp. 4263-4272.
Pop-Vicas A., et al, "The rising influx of multidrug-resistant gram-negative bacilli into a tertiary care hospital", Clin. Infect. Dis. 2005, vol. 40, pp. 1792-1798.
Prabhavathi F., "Antibacterial discovery and development—the failure of success", Nat. Biotechnol. 2006, vol. 24, pp. 1497-1503.
Saudek C, et al., "A Preliminary trial of the programmable implantable medication system for insulin delivery", N. Engl. J. Med., vol. 321, pp. 574-579 (1989).
Sefton M., "Implantable Pumps", CRC Critical Review Biomed. Eng., vol. 14, Issue 3, pp. 201-240 (1987).
Sun, J., et al., "Bacterial multidrug efflux pumps: mechanisms, physiology and pharmacological exploitations", Biochem. Biopysh. Res. Comm., pp. 254-267, vol. 453 (2014).
Treat, et al., "Liposome encapsulated docorubicin: preliminary results of phase I and phase II trials", Liposomes in the Therapy Infectious Disease and Cancer, pp. 353-365 (1989).
Vaara M., "Agents that increase the permeability of the outer membrane", Microbiol. Rev. 1992, vol. 56, pp. 395-411.
Vaara M., "Outer membrane permeability barrier to azithromycin, clarithromycin, and roxithromycin in gram-negative enteric bacteria", Antimicrob. Agents Chemother. 1993, vol. 37, pp. 354-356.
Van Bambeke, F., et al, "Inhibitors of bacterial efflux pumps as adjuvants in antibacterial therapy and diagnostic tools for detection of resistance by efflux", Fronteirs in anti-infective drug discovery, pp. 138-175 (2010).
Wang B, et al, "Antibacterial Diamines Targeting bacterial membranes", J.Med. Chem. 2016, vol. 59, pp. 3140-3151.
Wang C., et al, "Defining the molecular requirements for the selective delivery of polyamine conjugates into cells containing active polyamine trnasporters", J. Med. Chem. 2003, vol. 46, pp. 5129-5138.
Wang C., et al, "Molecular requirements for targeting the polyamine transport system. Synthesis and biological evaluation of polyamine-anthracene conjugates", J. Med. Chem. 2003, vol. 46, pp. 2672-2682.
Wang C., et al, "Pandrug-resistant pseudomonas aeruginosa among hospitalised patients: clinical features, risk-factors and outcomes", Clin. Microbiol. Infect. 2006, vol. 12, pp. 63-68.
Wang C., et al, "Synthesis and biological evaluation of N1-(anthracen-9-ylmethyl) triamines as molecular recognition elements for the polyamine transporter", J. Med. Chem. 2003, vol. 46, pp. 2663-2671.
Wieder T, et al, "Cyanine Dye Fluorescence used to measure membrane potential changes due to the assembly of complement proteins C5b-9", J. Membr. Biol. 1985, vol. 84, pp. 249-258.
Williams D., et al, "Motuporamines A-C, cytotoxic alkaloids isolated from the marine sponge *Xestospongia exigua* (kirkpatrick)", J. Org. Chem. 1998, vol. 63, pp. 4838-4841.
World Health Organization Report: antimicrobial resistance: global report on surveillance 2014. http://www.who.int/drugresistance/documents/surveillancereport/en/, 256 pages.

(56) References Cited

OTHER PUBLICATIONS

Wu M., et al, "Interaction of the cyclic antimicrobial cationic peptide bactenecin with the outer and cytoplasmic membrane", J. Biol. Chem. 1999, vol. 274, pp. 29-35.
Zasloff M., "Antimicrobial peptides of multicellular organisms", Nature 2002, vol. 415, pp. 389-395.

* cited by examiner

FIG. 7

Table1. MIC of motuporamine derivatives against various bacterial strains.

| Compound | MIC [μm] | | | | | | |
|---|---|---|---|---|---|---|---|
| | S.aureus ATCC25923 | S.intermedius 1051997 | E. faecalis ATCC29212 | E.coli ATCC 28922 | P.aeruginosa PAO1 | E. aerogenes EA289 | K.pneumoniae KPC2-ST258 |
| | | | | | | | |
| 7b, ANT4 | >200 | 200 | >200 | 200 | 200 | 100 | 100 |
| 7c, ANT44 | 50 | 200 | >200 | 50 | 100 | 200 | >200 |
| 7d, ANT444 | 12.5 | 25 | 200 | 25 | 100 | 100 | 100 |
| 7a, ANT-N-butyl | >200 | 200 | >200 | >200 | >200 | >200 | >200 |
| 6a, MOTU-CH$_2$-33 | 1.56 | 3.125 | 3.125 | 1.56 | 6.25 | 50 | 100 |
| 5a, MOTU-N33 | 3.125 | 1.56 | 12.5 | 3.125 | 12.5 | 100 | 100 |
| 6b, MOTU-CH$_2$-44 | 1.56 | 1.56 | 3.125 | 1.56 | 12.5 | 50 | 100 |
| 4b, MOTU44 | 100 | 50 | >200 | 100 | 100 | 50 | 100 |
| 4a, MOTU33 | 50 | 50 | 100 | 50 | 50 | 100 | 100 |
| 5b, MOTU-N44 | 1.56 | 1.56 | 6.25 | 6.25 | 25 | 50 | 50 |

FIG. 8

Table2. Concentration of motuporamine derivatives necessary to restore doxycycline activity (2µg/mL) against EA289, PAO1 and KPC2 ST258 Gram-negative bacterial strains.

| Compound | Concentration of motuporamine derivative [µm] | | |
|---|---|---|---|
| | EA289 | PAO1 | KPC2 ST258 |
| 7c, ANT44 | 10 | 5 | 5 |
| 7d, ANT444 | 1.25 | 2.5 | 1.25 |
| 4a, MOTU33 | 2.5 | 1.25 | 1.25 |
| 4b, MOTU44 | 1.25 | 2.5 | 1.25 |
| 5a, MOTU-N33 | 2.5 | 2.5 | 2.5 |
| 5b, MOTU-N44 | 5 | 1.25 | 2.5 |
| 6a, MOTU-CH$_2$-33 | 5 | 5 | 2.5 |
| 6b, MOTU-CH$_2$-44 | 2.5 | 2.5 | 1.25 |
| 7b, ANT4 | 40 | >40 | 40 |
| 7a, ANT-*N*-butyl | >40 | >40 | >40 |

MICs of doxycycline against PAO1, EA289, KPC2ST258: 40µg/mL (90µm), 20µg/mL (45µm), and 10µg/mL (22.5µm), respectively.

FIG. 9

Table 3. Concentration of the motuporamine derivative [μm] required to restore chloramphenicol, erythromycin, and cefepime activity (2μg/mL) against EA289, PAO1, and KPC2 ST258.

| Compound | PAO1 | | | EA289 | | | KPC2 ST258 | | |
|---|---|---|---|---|---|---|---|---|---|
| | CHL | ERY | FEP | CHL | ERY | FEP | CHL | ERY | FEP |
| 4a, MOTU33 | 5 | 20 | n.t. | 40 | 40 | 40 | 40 | >40 | >40 |
| 4b, MOTU44 | 5 | 40 | n.t. | 40 | >40 | >40 | 40 | >40 | >40 |
| 5a, MOTU-N33 | 2.5 | 10 | n.t. | 20 | 20 | 20 | 20 | 40 | >40 |
| 5b, MOTU-N44 | 5 | >40 | n.t. | >40 | 40 | >40 | 40 | >40 | 40 |
| 6b, MOTU-CH$_2$-44 | 2.5 | 10 | n.t. | 20 | 20 | >40 | 20 | >40 | >40 |

CHL: chloramphenicol, ERY: erythromycin, FEP: cefepime, n.t.: not tested. MIC of FEP against PAO1: 10 μg/mL. All other antibiotic/strain combinations: >100 μg/mL.

MOTUPORAMINE DERIVATIVES AS ANTIMICROBIAL AGENTS AND ANTIBIOTIC ENHANCERS AGAINST RESISTANT GRAM-NEGATIVE BACTERIA

BACKGROUND

Antimicrobial resistance threatens the prevention and treatment of an ever-increasing range of infections caused by bacteria, parasites, viruses, and fungi. An increasing number of governments around the world are devoting efforts to this problem, which is so serious that it threatens the achievements of modern medicine. Far from being an apocalyptic fantasy, a post-antibiotic era in which common infections and minor injuries can kill is a real possibility for the 21st century. A recent WHO report makes a clear case that resistance to common bacteria has reached alarming levels in many parts of the world, and that in some settings few, if any, of the available treatment options remain effective for common infections. Another important finding of the report is that surveillance of antibacterial resistance is neither coordinated nor harmonized and there are many gaps in information regarding bacteria of major public health importance.[1]

The intensive use of antibiotics for the treatment of numerous bacterial infections is one of the biggest healthcare advances in modern times. Nevertheless, their widespread use has led to an increasing number of antibiotic-resistant bacteria.[2] In particular, the emergence of Gram-negative multidrug-resistant (MDR) bacteria, such as Pseudomonas aeruginosa and Klebsiella pneumoniae, has prompted efforts to develop new classes of antibiotics and chemosensitizers (molecules to promote an increase in the internal antibiotic concentration in resistant strains). Thus, diseases caused by MDR Gram-negative bacteria are increasing worldwide,[3,64] and the emergence of pan drug-resistant (PDR) bacteria (resistant to all classes of antibiotics and to quaternary ammonium disinfectants)[5] appears to have reached a point of no return.[6,7] A great concern has been noticed in the medical community, as numerous recent clinical reports have confirmed that Gram-negative bacteria have developed resistance to polymyxins, the last efficient therapy against PDR Gram-negative bacteria.[8-10]

An appealing target is the unique structure of the bacterial membrane, which is highly conserved among most species of Gram-negative bacteria, and forms an effective barrier to many types of antibiotics.[11] Indeed, the acquisition of resistance to membrane-active antibiotics has likely required major changes in membrane structure. Ironically, modifications to the bacterial membrane to escape membrane-targeting antibiotics might increase the permeability of the barrier and actually increase the susceptibility of the bacteria to hydrophobic antibiotics.

It is well established that most immune responses to Gram-negative bacteria involve recognition of lipopolysaccharides (LPS) and their lipid-A anchors, which constitute the major components of the outer membrane.[12-17] The permeability barrier of the outer membrane is due to the cross-bridging electrostatic interactions between lipid-A molecules and divalent cations such as calcium or magnesium.[12] It was speculated that cationic peptides[18] and polyamines[19] could out-compete these divalent cations for their membrane binding sites and disrupt the outer membrane organization, thereby increasing permeability. Because of the promising applications of polyamine derivatives in medicine,[20-22] a series of hydrophobic polyamine derivatives have been evaluated for their ability to target the membrane stability of Gram-negative bacteria and increase the sensitivity of these bacteria to known antibiotics.

SUMMARY

The motuporamines (originally isolated from the marine sponge Xestospongia exigua)[23] were selected because their amphiphilic architectures comprise a large hydrophobic macrocycle with an appended polyamine motif (1-3, Schemel, FIG. 6). A series of motuporamine derivatives (4-6) was prepared[24,25] along with a series of related anthracenyl-polyamine derivatives (7a-d). These amphiphilic polyamines have large hydrophobic substituents to facilitate interaction with the bacterial membrane.

Here, 4-6 and 7a-d were screened for their in vitro antimicrobial activities and antibiotic-enhancement properties against resistant Gram-negative bacteria. The mechanism of action of this class of derivatives was also tested against Enterobacter aerogenes (EA289) by using fluorescent dyes, in order to evaluate changes in outer-membrane depolarization and permeabilization.

In addition, compounds 8a, 8b, 9a, 9b, 10, 11a, 11b, 11c, 12a, and 15, structures provided below are included as agents to alleviate antibiotic resistance.

In addition, cholic acid has been shown to assist the orientation of membrane-disrupting agents (REF: Bioconjugate Chem. 2016, 27, 2850-2853) and according to another embodiment, a special fifteen membered macrocycle of the motuporamine scaffold was used to design and produce new membrane targeting compounds (e.g., 16a-c) as antibiotic agents or as adjuvants for known antibiotics or as potential anti-metastatic agents for oncologic applications.

In addition, another motuporamine derivative antibiotic agent disclosed herein is compound 50.

BRIEF DESCRIPTION OF DRAWINGS

FIG. 7 Table 1-MIC of motuporamine derivatives against various bacterial strains.

FIG. 8 Table 2-Concentration of motuporamine derivatives necessary to restore doxycycline activity (2 µg/mL) against EA289, PAO1 and KPC2 ST258 Gram-negative bacterial strains.

FIG. 9 Table 3-Concentration of the motuporamine derivative [μm] required to restore chloramphenicol, erythromycin, and cefepime activity (2 μg/mL) against EA289, PAO1, and KPC2 ST258.

DEFINITIONS

Figure 1:
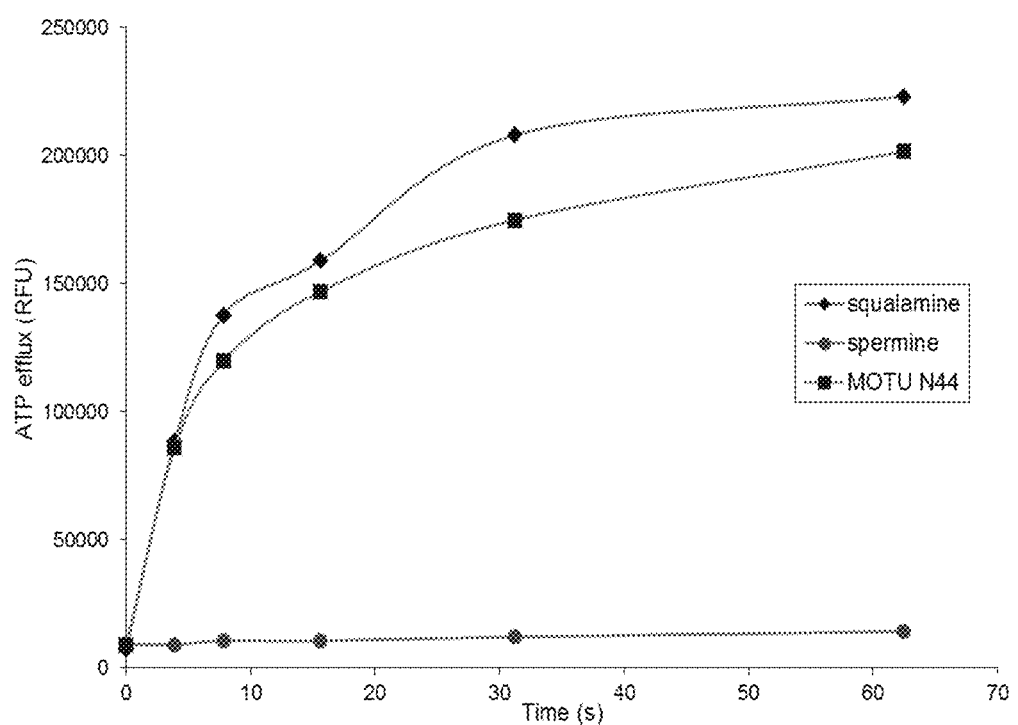
FIG. 1 The effect of squalamine (100 µg/mL), spermine (100 µg/mL), and 5b (MOTU-N44, 100 µg/mL) on ATP release kinetics for Gram-positive bacteria S. aureus.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents, "administration" and its variants are each understood to include concurrent and sequential introduction of the compound or prodrug thereof and other agents.

The term "antibiotic" or "conventional antibiotic" refers to antibiotic agents historically used to treat bacteria. Examples of conventional antibiotics include, but are not limited to, amoxicillin, doxycycline, erythromycin, chloramphenicol, cephalexin, ciprofloxacin, clindamycin, methicillin, metronidazole, penicillin, rifampicin, azithromycin, sulfamethoxazole/trimethoprim, amoxicillin/clavulanate, levofloxacin, or vancomycin. Other examples of conventional antibiotics include Ampicillin, Vancomycin, Gentamicin, Tetracycline, Rifampin, Norfloxacin, Rifaximin, Tigecycline, Furazolidone, Triclosan, Cefoperazone, Silver sulfadiazine, Dapsone, Gemifloxacin, Sulfadimidine, Enoxacin, Sulfisoxazole, Ceftolozane, Prontosil, Sulfapyridine, Sulfamerazine, Grepafloxacin, Sulfamethoxypyridazine, Sulfalene, Acetic acid/hydrocortisone, Sulfaphenazole, Sulfametoxydiazine, Sulfamoxole, Sulfabenzamide, Sulfametrole, Viridicatumtoxin B, Sulfametomidine, Sulfaperin, or Sulfathiourea.

The term "coadministering" or "concurrent administration", when used, for example with respect to administration of a polyamine compound along with administration of a antibiotic refers to administration of the polyamine compound and the antibiotic such that both can simultaneously achieve a physiological effect. The two agents, however, need not be administered together. In certain embodiments, administration of one agent can precede administration of the other, however, such coadministering typically results in both agents being simultaneously present in the body (e.g. in the plasma). Coadministration allows for administration at a significant fraction (e.g. 20% or greater, preferably 30% or 40% or greater, more preferably 50% or 60% or greater, most preferably 70% or 80% or 90% or greater) of their maximum serum concentration for any given dose to still enable therapeutic efficacy.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to a microbial infection, an effective amount comprises an amount sufficient to kill or inhibit the growth and replication of the microbe. In some embodiments, an effective amount is an amount sufficient to delay development. In some embodiments, an effective amount is an amount sufficient to prevent or delay occurrence and/or recurrence. An effective amount can be administered in one or more doses.

As used herein, "treatment" refers to obtaining beneficial or desired clinical results. Beneficial or desired clinical results include, but are not limited to, any one or more of: alleviation of one or more symptoms, diminishment of extent of infection, stabilization (i.e., not worsening) of the state of infection, preventing or delaying spread of the disease (such as pathogen growth or replication), preventing or delaying occurrence or recurrence of the disease, delay or slowing of disease progression and amelioration of the disease state. The methods of the invention contemplate any one or more of these aspects of treatment.

A "subject in need of treatment" is a mammal with a microbial infection that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a. suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc, Examples of suitable pharmaceutical carriers are described in "Remington's Pharmaceutical Sciences" by E. W. Martin. Such compositions will contain a therapeutically effective amount of the compound together with a suitable amount of carrier so as to provide the form for proper administration to the patient. The formulation should suit the mode of administration.

DETAILED DESCRIPTION

It has been discovered that certain lipophilic polyamines can serve as antimicrobial agents or as antibiotic enhancers. In addition, the compounds described herein can ameliorate antibiotic resistance of many antibiotics against microbes such as bacteria, and Gram-negative bacteria in particular. Examples of compounds useful for this purpose include those of the following formula:

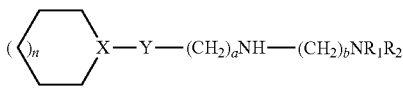

where n=1-13; X=N or CH; Y=CH$_2$ or N; a=0-8; b=0-8; R$_1$=H or alkyl (e.g., Me or Et or i-Pr or propyl or butyl or t-butyl) or alkylamino (e.g. (CH$_2$)$_m$NH$_2$, where m=2-8) or alkyl-N-alkylamino (e.g., (CH$_2$)$_m$NHMe, where m=2-8) or alkylpolyamino (e.g., (CH$_2$)$_m$NH(CH$_2$)$_p$NHR, where m and p=2-8 and R=H or alkyl).

Another aspect of the invention is in the formula:

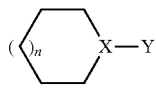

where n=1-13; X=N or CH; Y=alkylalcohol ((e.g. (CH$_2$)$_m$OH, where m=2-8) or alkyl-O-alkylamino (e.g., (CH$_2$)$_m$OMe, where m=2-8) or polyether (e.g., (CH$_2$)$_m$O(CH$_2$)$_p$OH or polyvinylether), or or alkylamide (e.g., (CH$_2$)$_m$NHCOCH$_3$, where m=2-16) or when X=CH the macrocycle is attached to Y which is either an amine or amide linkage connecting a cholic acid derivative (—NH(CH$_2$)$_z$NH-cholic acid scaffold, where z=2-16, see example structures 16a-c below) or a pharmaceutically acceptable salt thereof.

Specific examples of such lipophilic polyamines include 4a, 4b, 5a, 5b, 6a, 6b, 7a, 7b, 8a, 8b, 9a, 9b, 10, 11a, 11b, 11c, 12a, and 15 described further herein. According to further specific embodiments, fifteen membered rings as either carbocycles or N-based heterocycles are implemented.

Specific Examples

4a: X=N; Y=CH$_2$; a=2; b=3; R$_1$=R$_2$=H
4b: X=N; Y=CH$_2$; a=3; b=4; R$_1$=R$_2$=H
4c: X=N; Y=CH$_2$; a=2; b=3; R$_1$=Me; R$_2$=H
4d: X=N; Y=CH$_2$; a=3; b=4; R$_1$=Me; R$_2$=H
4e: X=N; Y=CH$_2$; a=2; b=3; R$_1$=R$_2$=Me
4f: X=N; Y=CH$_2$; a=3; b=4; R$_1$=R$_2$=Me
5a: X=CH; Y=N; a=3; b=3; R$_1$=R$_2$=H
5b: X=CH; Y=N; a=4; b=4; R$_1$=R$_2$=H
5c: X=CH; Y=N; a=3; b=3; R$_1$=Me; R$_2$=H
5d: X=N; Y=CH2; a=2; b=3; R$_1$=Me; R$_2$=H
5e: X=CH; Y=N; a=3; b=3; R$_1$=R$_2$=Me
5f: X=CH; Y=N; a=4; b=4; R$_1$=R$_2$=Me
6a: X=CH; Y=CH$_2$; a=0; b=3; R$_1$=(CH$_2$)$_3$NH$_2$; R$_2$=H
6b: X=CH; Y=CH$_2$; a=0; b=4; R$_1$=(CH$_2$)$_4$NH$_2$; R$_2$=H
6c: X=CH; Y=CH$_2$; a=0; b=3; R$_1$=(CH$_2$)$_4$NH$_2$; R$_2$=H
6d: X=CH; Y=CH$_2$; a=0; b=4; R$_1$=(CH$_2$)$_3$NH$_2$; R$_2$=H
6e: X=CH; Y=CH$_2$; a=0; b=3; R$_1$=(CH$_2$)$_4$NHMe; R$_2$=H
6f: X=CH; Y=CH$_2$; a=0; b=4; R$_1$=(CH$_2$)$_3$NHMe; R$_2$=H
6g: X=CH; Y=CH$_2$; a=0; b=4; R$_1$=(CH$_2$)$_3$NHMe; R$_2$=H
6h: X=CH; Y=CH$_2$; a=0; b=4; R$_1$=(CH$_2$)$_4$NHMe; R$_2$=H
6i: X=CH; Y=CH$_2$; a=0; b=3; R$_1$=(CH$_2$)$_4$NH(CH2)$_3$NH$_2$; R$_2$=H
6j: X=CH; Y=CH$_2$; a=0; b=3; R$_1$=(CH$_2$)$_4$NH(CH2)$_3$NHMe; R$_2$=H
11a: X=CH; Y=CH$_2$; a=0; b=2; R$_1$=(CH$_2$)$_2$NH$_2$; R$_2$=H
11b: X=CH; Y=CH$_2$; a=0; b=2; R$_1$=R$_2$=H
11c: X=CH; Y=CH$_2$; a=0; b=2; R$_1$=(CH$_2$)$_2$NH(CH2)$_2$NH$_2$; R$_2$=H

Other examples include:

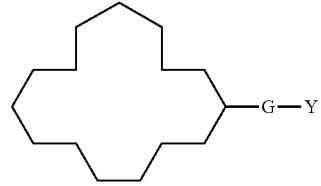

where G=(CH$_2$)$_x$ where x=0-12 and Y is an attached cholic acid via an amide or amine linkage

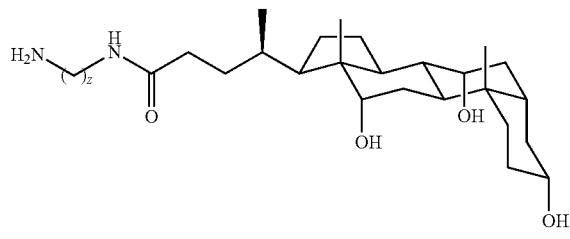

cholic acid derivative

-continued

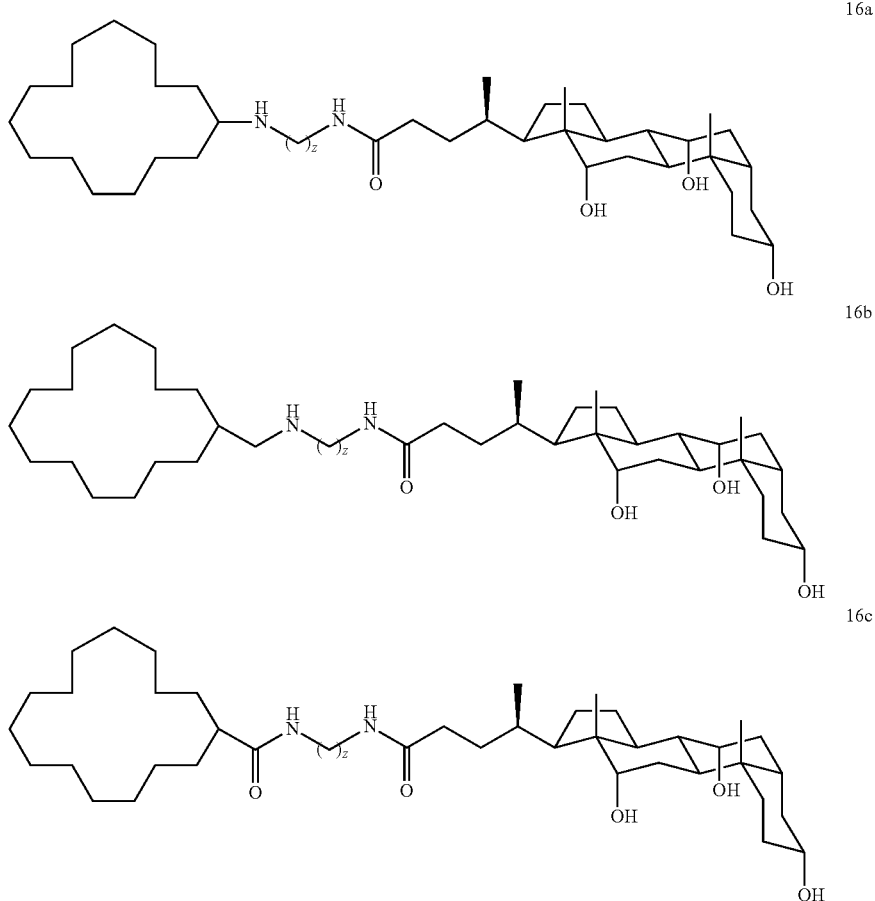

z = 2-16

Moreover, another example includes the following:

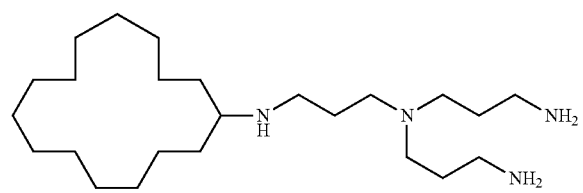

According to certain embodiments, provided is a method of treating a microbe infection, or reducing antibiotic resistance of microbes comprising contacting said microbes with an effective amount of one or more compounds selected from the group consisting of 4a, 4b, 5a, 5b, 6a, 6b, 7a, 7b, 8a, 8b, 9a, 9b, 10, 11a, 11b, 11e, 12a, 15, 16 and 50.

Another embodiment pertains to a method of treating an infection in a subject comprising coadministering an effective amount of one or more compounds selected from the group consisting of 4a, 4b, 5a, 5b, 6a, 6b, 7a, 7b, 8a, 8b, 9a, 9b, 10, 11a, 11b, 11e, 12a, 15, 16 and 50; and an effective amount of an antibiotic. The antibiotic may include amoxicillin, doxycycline, erythromycin, chloramphenicol, cephalexin, ciprofloxacin, clindamycin, methicillin, metronidazole, penicillin, rifampicin, azithromycin, sulfamethoxazole/trimethoprim, amoxicillin/clavulanate, levofloxacin, or vancomycin or a combination thereof. In addition to the preceding, or alternatively, the antibiotic includes Ampicillin, Vancomycin, Gentamicin, Tetracycline, Chloramphenicol, Rifampin, Norfloxacin, Rifaximin, Tigecycline, Furazolidone, Triclosan, Cefoperazone, Silver sulfadiazine, Dapsone, Gemifloxacin, Sulfadimidine, Enoxacin, Sulfisoxazole, Ceftolozane, Prontosil, Sulfapyridine, Sulfamerazine, Grepafloxacin, Sulfamethoxypyridazine, Sulfalene, Acetic acid/hydrocortisone, Sulfaphenazole, Sulfametoxydiazine, Sulfamoxole, Sulfabenzamide, Sulfametrole, Viridicatumtoxin B, Sulfametomidine, Sulfaperin, or Sulfathiourea, or a combination thereof.

Other embodiments pertain to a composition comprising a combination of an effective amount of one or more polyamine compounds selected from the group consisting of 4a, 4b, 5a, 5b, 6a, 6b, 7a, 7b, 8a, 8b, 9a, 9b, 10, 11a, 11b, 11e, 12a, 15, 16, and 50; and an effective amount of an antibiotic. The composition may further include a pharmaceutically effective carrier. The one or more compounds may include derivatives or pharmaceutically acceptable salts thereof.

Combining one or more polyamine compounds with antibiotics as taught herein enables the reduction in doses of both the polyamine compound and antibiotic to ameliorate potential adverse side effects. Accordingly, methods that involve the coadministering of compounds or compositions comprising a combination can be provided wherein the antibiotic is effective at a lower dosage in combination with the one or more compounds than without the one or more compounds.

Appendix A is provided as background information concerning the structures and methods of making polyamine compounds described herein. Appendix B sets forth further data and information on polyamine compounds that can be used as antimicrobials or antibiotic enhancers as described herein. Further background information regarding polyamine compounds useful as antimicrobials or antibiotic enhancers is found at U.S. Pat. Nos. 9,346,741; 9,212,131; 9,150,495; 8,497,398; 7,910,363; 7,728,041; 7,728,040; and 7,001,925. The disclosures of any references cited herein are incorporated in their entirety herein to the extent not inconsistent with the teachings herein.

In a broader context, what is contemplated is the use of the compounds of the invention to attenuate antibiotic resistance and/or bacterial virulence. In one embodiment, the compound or compounds are a component of a composition and have efficacy to inhibit antibiotic resistance and/or bacterial virulence, preferably of Gram negative bacteria, such as, for example, *P. aeruginosa*. Preferably these compositions comprise a lipophilic polyamine, or derivatives thereof, or pharmaceutically acceptable salts thereof. In another embodiment procedures are contemplated comprising administering lipophilic polyamines or derivatives, or the compositions to an individual who is free of bacterial disease. Preferably, administration is in advance of an anticipated health-related procedure known to increase susceptibility to a Gram negative bacteria, and preferably, *P. aeroginosa* pathogenicity, for example, in advance of a surgical procedure, including dental procedures, especially procedures involving implants, or insertion of catheters or other devices. In yet another embodiment, it is contemplated to contact surfaces of work areas, medical instruments, medical devices and the like with the compositions of the invention in order to attenuate the antibiotic resistance and/or virulence of a Gram negative bacteria, such as *P. aeroginosa*, that might come into contact with these surfaces.

In another aspect of the invention, embodiments pertain to deploying the compounds of the invention to prevent the failure of devices that are prone to fouling by biofilms. These compounds are useful in industrial settings and in contexts requiring medical implants. The compounds of the invention may be administered in the liquid phase, may be embedded in materials used for production of such devices, or may coat such devices resulting in products that are innately resistant to biofilms. These compounds also may be used to inhibit biofilms from forming in situations where liquids are flowing, as, for example, through pipes, pipelines, tubing, water cooling systems, stents or filtration devices.

Indications

Gram negative bacteria are typically free-living organisms often found in soil and water, and play an important role in decomposition, biodegradation, and the C and N cycles. However, many Gram negative bacteria are pathogenic. Examples of Gram negative bacteria that can be inhibited by compounds of the invention, include, but are not limited to *Burkholderia cepaci, C. violaceum, harveyi, Staphylococcus* including but not limited to, *S. aureus* and *S. intermedius, Pseudomonas*, including, but not limited to *Pseudomonas aeruginosa, Neisseria gonorrhoeae, Neisseria meningitidis, Bordetella pertussis, Haemophilus influenzae, Legionella pneumophila, Brucella, Francsella, Xanthomonas, Agrobacterium*, enteric bacteria, such as *Escherichia coli* and its relatives, *Enterobacter aerogenes*, the members of the family Enterobacteriaceae, such as *Salmonella* and *Shigella, Proteus*, and *Yersinia pestis*.

For example, Gram negative bacteria often cause opportunistic infections in immune-compromised or immune-suppressed individuals. One example of such a bacteria is *P. aeruginosa*. These infections are spread by heath care workers or patients to surfaces, machinery or instruments in health care facilities. *P. aeruginosa* typically infects the pulmonary tract, urinary tract, burns, and wounds. *P. aeruginosa* also causes catheter-associated infections, blood infections, middle ear infections, formation of dental plaque, gingivitis, chronic sinusitis, endocarditis, coating of contact lenses, and infections associated with implanted devices, for example, catheters, joint prostheses, prosthetic cardiac valves and intrauterine devices. *P. aeruginosa* causes infections of the central nervous system, gastrointestinal tract, bones, joints, ears and eyes. The compounds or compound compositions of the invention can be used to treat these infections and conditions.

Specifically, the compound or compound compositions of the invention can be administered alone or in combination with conventional antibiotics, to treat, inhibit, and/or ameliorate infections including opportunistic infections and/or antibiotic resistant bacterial infections caused by gram negative bacteria. Examples of such opportunistic infections, include, but are not limited to *P. aeruginosa*. or polymicrobial infections of *P. aeruginosa* with, for example, *Staphylococcus aureus* or *Burkholderia cepacia*. Examples of patients, who may acquire such opportunistic and/or resistant infections include, but are not limited to patients who are immune-compromised or immune-suppressed, who have cystic fibrosis or HIV or who have implanted medical devices, subcutaneous devices or who are on ventilators, patients who have been intubated or who have catheters, nosocomial infections, patients who are undergoing bone marrow transplant or other types of surgery, including, but not limited to dental surgery and patients who are intravenous drug users, especially with regard to heart valve infection.

Burns and/or other traumatic wounds as well as common or uncommon infections can also be prophylactically treated and/or ameliorated by administration of the compound or compound compositions. Examples of such wounds and infection disorders include, but are not limited to puncture wounds, radial keratotomy, ecthyma gangrenosum, osteomyelitis, external otitis or dermatitis.

In one embodiment, the compound or compound compositions of the invention can be administered to treat, prevent, and/or ameliorate pulmonary infections. More preferably, the compound or compound compositions of the invention can be administered to treat, prevent, diagnose, and/or ameliorate pneumonia. More preferably, the compound or compound compositions of the invention can be administered to treat, prevent, and/or ameliorate lung infections, such as pneumonia, in cystic fibrosis patients. More preferably, the compound or compound compositions of the invention can be administered to treat, prevent, and/or ameliorate Gram negative infections such as by *P. aeruginosa* in cystic fibrosis patients. Pneumonia can be caused by colonization of medical devices, such as ventilator-associated pneumonia, and other nosocomial pneumonia, and the compound or compound compositions of the invention can be administered to treat and/or prevent these types of pneumonia or bacterial infections as well.

Additionally, the compound or compound compositions of the invention can be administered to treat and prevent septic shock. More preferably, the compound or compound compositions of the invention can be administered to treat, prevent, and/or ameliorate septic shock in neutropenic, immune-compromised, and/or immune-suppressed patients or patients infected with antibiotic resistant bacteria, such as, for example, antibiotic resistant *P. aeruginosa*.

Additionally, the compound or compound compositions of the invention can be administered to treat, prevent, and/or ameliorate urinary tract or pelvic infections. In another preferred embodiment, the compound or compound compositions of the invention can be administered to treat, prevent, and/or ameliorate gastrointestinal infections, such as necrotizing enterocolitis, often seen in premature infants and/or neutropenic cancer patients.

Additionally, the compound or compound compositions of the invention can be administered to treat, prevent, and/or ameliorate urinary dysenteriae (for example, dysenteria caused by bacillary dysentery), food poisoning and/or gastroenteritis (for example, caused by *Salmonella enterica*), typhoid fever (for example, caused by *Salmonella typhi*), whooping cough (or pertussis) as is caused by *Bordetella pertussis*, Legionnaires' pneumonia, caused by *Legionella pneumophila*, sexually transmitted diseases, such as gonorrhea, caused by *Neisseria gonorrhoeae*, or meningitis, caused by, for example, *Neisseria meningitidis* or *Haemophilus influenzae*, brucellosis which is caused by brucellae, and more specifically, *Brucella abortus*.

Formulations and Methods of Administration

The invention provides methods of treatment, inhibition and prophylaxis by administration to a subject of an effective amount of the compound or a pharmaceutical composition of the invention. In a preferred aspect, the compound is substantially purified (i.e., substantially free from substances that limit its effect or produce undesired side-effects). The subject is preferably an animal, and preferably a mammal, including but not limited to animals such as cows, pigs, horses, chickens, cats, dogs, etc., and is most preferably a human.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

For topical administration, the present compounds may be applied in pure-form, i.e., when they are liquids. However, it will generally be desirable to administer them to the skin as compositions or formulations, in combination with a dermatologically-acceptable carrier, which may be a solid or a liquid. Based on the discoveries noted herein, the compounds described herein can be used to promote healing by providing a bacteria reduced environment for wound closure and rapid healing.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (U.S. Pat. No. 4,938,949 (Borch et al.)).

Accordingly, the invention includes a pharmaceutical composition comprising a compound of the present invention as described above, or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

Formulations and methods of administration that can be employed with the compound or compound compositions, additional appropriate formulations and routes of administration can be selected from among those described herein below. The compound or compound compositions of the invention may be administered therapeutically, such as, for example, in the case of infection of a susceptible patient with burn or other traumatic wound injury or lung infection, such as in a cystic fibrosis patient infected with *P. aeruginosa, S. Aureus*, or *E. aerogenes* separately or in combination. Alternatively, the compound or compound compositions may be administered prophylactically, such as, for example, to prevent opportunistic Gram negative bacterial infection, such as by *P. aeruginosa*, prior to surgery, dental work, or implantation of a medical device such as a catheter or ventilator tube continuously, such as, for example in the case of an immune-suppressed or immune-compromised patient.

Various alternative delivery systems are known and can be used to administer compound, e.g., encapsulation in liposomes, microparticles, microcapsules. Methods of introduction include, but are not limited to, topical, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of art inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the composition can be delivered in a vesicle, in particular a liposome (see Langer, Science 249:1527-1533 (1990); Treat et al, in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release system. In one embodiment, a pump may be used (see Langer, supra; Sefton, CRC Crit, Ref Biomed. Eng. 14:20 1 (1987); Buchwald et al, Surgery 88:507 (1980); Saudek et al, N. Engl. J. Med. 321:574 (1989)), In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, Macromol. Sci. Rev. Macromol. Chem. 2.3:61 (1983); see also Levy et al, Science 2.28:190 (1985); During et al, Ann. Neurol. 25:35 1 (1989); Howard et al, J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The present invention also provides pharmaceutical compositions. Such compositions comprise a therapeutically effective amount of compound and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

In a typical embodiment, the composition is formulated in accordance with routine procedures as a pharmaceutical composition adapted for intravenous, topical or pulmonary administration to human beings. Typically, compositions for such administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms, Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention that will be effective in the treatment, inhibition and prevention of a disease or disorder can be determined by standard clinical techniques. Additionally, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For example, the dosage administered to a patient should typically be 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. In preferred embodiments, a dose of 1, 4, 10, or 20 mg/kg is administered intravenously to a patient. Further, the dosage and frequency of administration, of therapeutic or pharmaceutical compositions of the invention may be reduced by enhancing uptake and tissue penetration (e.g., into the skin and/or lungs) of by modifications such as, for example, lipidation.

The compound or compound compositions of the invention may be administered alone or in combination with other compounds, such as adjuvants. In one embodiment the compounds may be administered in combination with one or more antibiotics, for example, gentamicin, tobramycin, colistin, and fluoroquinolones. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In the treatment of burns or other traumatic wound injuries that are susceptible to bacterial infection such as, for example, P. aeruginosa infection, the presently described compound can be prepared in a medicament and the preparation applied generously (e.g., topically) to the entire burn area as quickly as possible. Repeated applications are made, if necessary and as needed to relieve pain, increase healing and decrease infection. If necessary, resuscitation is started by the introduction of the conventional intravenous fluids. Pain killers, toxin neutralizers, vitamins and antibiotics may be employed as indicated. Moreover, intravenous treatment of the compound or compound composition may also be needed to treat the burn or other traumatic wound injury.

The wound to which the compound or compound compositions have been applied may be covered with gauze and sheet wadding and thereafter dressed daily. At the time of dressing, all devitalized tissue and crusts, which can be removed readily, should be removed. Tissue, which is attached firmly, is permitted to separate normally.

In the use of the compound or compound compositions for the treatment of lung infections, preferably, for example, in patients suffering from cystic fibrosis, pneumonia (regardless of the etiology), and/or antibiotic resistant bacterial pulmonary infection, the compound will generally be administered for symptomatic treatment in the form of a conventional pharmaceutical composition, for example, as generally described in U.S. Pat. No. 4,910,190, and preferably as an aerosol. A formulation providing a solution containing a concentration, for example, of 10 mg/mL, 20 mg/mL, or 30 mg/mL of the compound and suitable for use with a nebulizer (preferably) or as an injectable solution. A suitable nebulizer for use is, for example, a RETEC™ nebulizer, in which the solution is nebulized with compressed air.

In general, the compound or compound compositions will be administered to humans at a daily dose in the range of, for example, 5 to 100 mg of the compound by aerosol or 50 to 1000 mg intravenously, or a combination of the two. However, it readily will be understood that it may be necessary to vary the dose of therapeutic product administered in accordance with well-known medical practice to take account of the nature and severity of the lung disease (for example, cystic fibrosis) under treatment, concurrent therapy, and the age, weight and sex of the patient receiving treatment. It similarly will be understood that generally equivalent amounts of a pharmaceutically acceptable salt of the compound also may be used. It is noted that oral formulations may work via systemic effects.

EXAMPLES

Example 1: Antimicrobial Activity

Results and Discussion

Investigations began with the determination of the minimum inhibitory concentrations (MICs) of 4-7 in Gram-positive and -negative species, in order to identify the concentrations that produce a direct antibacterial effect and allowed us to rank their relative potencies. Included were two Gram-negative bacteria encountered in hospitals, *P. aeruginosa* and *Klebsiella pneumonia*, and multidrug-resistant *E. aerogenes* EA289 (Table1). Several compounds showed MICs of 100-200 µM for these bacterial strains. The anthracenyl compounds 7a-d had relatively weak antimicrobial activities, whereas their related motuporamine derivatives 4a-b, 5a-b, and 6a-b showed MICs of 1.56-50 µM. Specifically, 6a (MOTU-CH$_2$-33) and 6b (MOTU-CH$_2$-44) exhibited excellent antimicrobial activities against many species, including the multidrug-resistant *E. aerogenes* EA289.

As stated previously, the development of chemo-sensitizing agents, which enhance the intracellular antibiotic concentration in resistant strains (or by other mechanisms) is an attractive approach to overcome bacterial resistance. Thus, investigated was the use of these polyamine derivatives as adjuvants in combination with antibiotics. Success here would provide an exciting approach to increase the potency of current antibacterial drugs, even for strains that have developed resistance.

It was investigated whether these polyamine agents could restore the potency of the antibiotic doxycycline at significantly below its MIC. For example, it was found that the MIC of doxycycline against P. aeruginosa PAO1 was 16 µg/mL, so investigated was the use of doxycycline at a significantly lower concentration (2 µg/mL, corresponding to its pharmacokinetic properties in humans)[6] in the presence of the polyamine derivatives. It was believed that the polyamine agents would disrupt bacterial membrane integrity and increase antibiotic delivery to the bacteria and thus increase doxocycline potency. Rewardingly, even at this low doxycycline concentration, eight of the polyamine derivatives restored doxycycline activity against E. aerogenes EA289, P. aeruginosa PAO1, and K pneumoniae KPC2-ST258; no improvement was observed for 7b (ANT4) or 7a (ANT-N-butyl) even at 40 µM (Table2). The fact that this effect was compound-specific was intriguing and ruled out a non-specific detergent effect, especially because no cell lysis was observed.

Several of the effective compounds also acted synergistically with chloramphenicol and erythromycin, particularly against PAO1, but weakly against EA289 and KPC2-ST258 (Table3). Thus, two groups of compounds were identified: one (7a and 7b) displayed weak or no activity, and the second (e.g., 5a and 5b) increased the antibiotic susceptibility effectively against PAO1. Overall, 5a and 5b appeared the most promising adjuvants for use with doxycycline; 5b (MOTU-N44) was chosen to investigate the mechanism of action of this molecular class.

Within the motuporamine series (4-6) several compounds exhibited moderate to good antibacterial activity as well as potent synergy with different antibiotics against Gram-negative bacteria. The mechanism of action of these compounds was explored and focused on two possible pathways: permeabilization and/or disruption of the outer membrane, and inhibition of an efflux pump.

First, the effect of 5b on *Staphylococcus aureus* ATCC25923 was determined by measuring ATP release for 1 min: there was dramatic disruption of the bacterial membrane, similar to that by squalamine (positive control; FIG. 1 Conversely, no significant effect was found for the polyamine spermine (negative control).

Since different compound performance was observed in the assays with *S. aureus* in Table 1, it was believed that some of these molecules may achieve lethality by increasing the rate of transport of molecules across the cytoplasmic membrane, while others may not. It was surmised that compounds like 5b may induce a smaller membrane breach, modestly affect the permeability barrier of the cytoplasmic membrane and cause membrane depolarization. Indeed, a small breach would allow passage of electric current (thereby causing membrane depolarization) without allowing passage of larger molecules. This alternative mechanism seemed plausible because depolarization would de-energize the efflux pump and also lead to increased potency of the antibiotic agent. Therefore, it was investigated whether these molecules generated a smaller breach of the permeability barrier of the cytoplasmic membrane.

Figure 2:
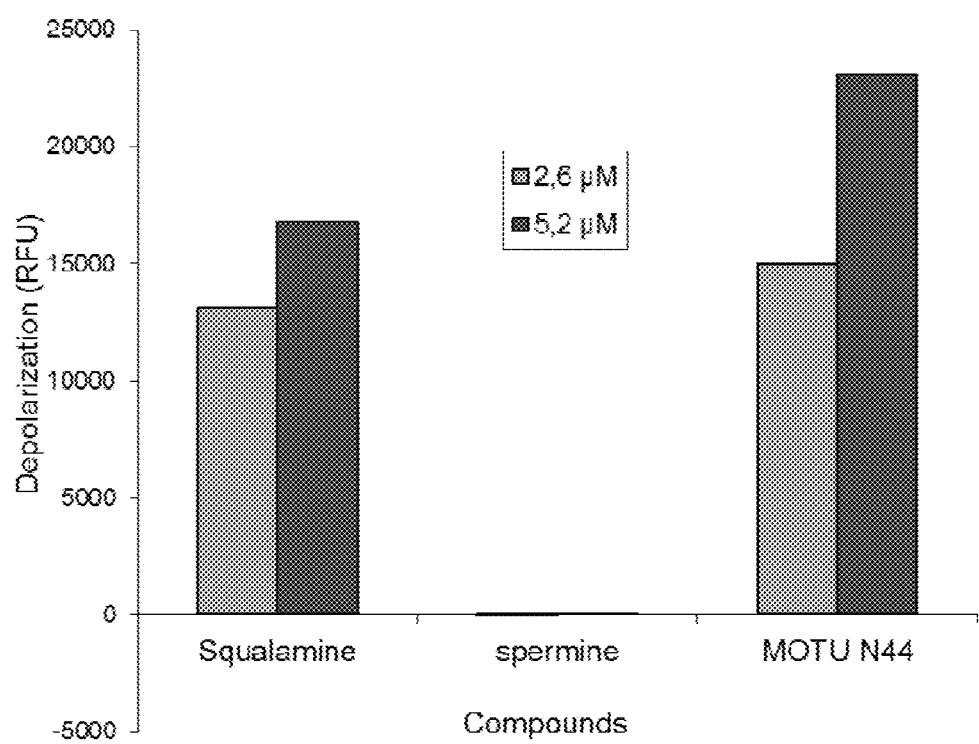
FIG. 2 Depolarization of the bacterial membrane of S. aureus in the presence of 2.6 and 5.2 µM squalamine, spermine, or 5b (MOTU-N44).

Fluorescent cyanine dyes are excellent probes to monitor membrane depolarization. These dyes lose fluorescence intensity when in polarized membranes and become highly fluorescent once polarization is lost. Thus, one can use changes in dye fluorescence to monitor change in membrane polarization. Interestingly, strong depolarization of *S. aureus* membranes was observed after 21 minutes as a strong increase in relative fluorescent units (RFU) of the cyanine dye (FIG. 2) in the presence of 5b. This suggests that 5b facilitated membrane depolarization.

Figure 3A:
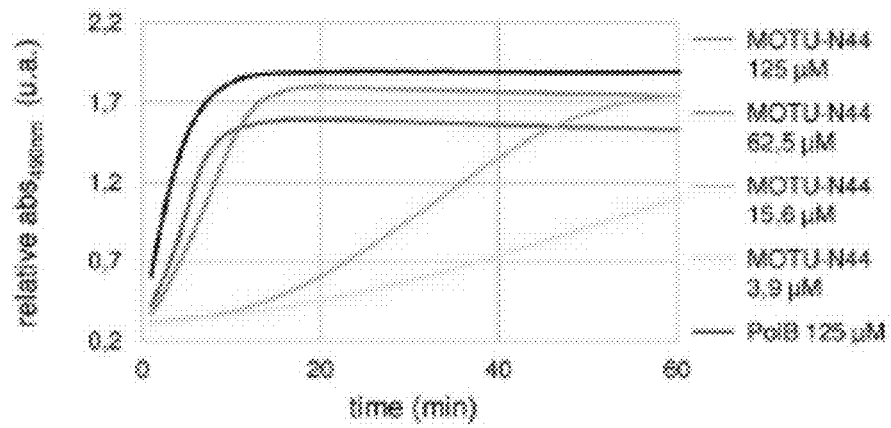
FIG. 3a) Outer-membrane permeabilization detected by nitroceflin hydrolysis, in a dose- and time-dependent manner.

Next, 5b was investigated for its ability to alter the cell outer membrane integrity of *E. aerogenes* EA289, by using nitrocefin, a chromogenic beta-lactam that is efficiently hydrolyzed by periplasmic beta-lactamases, thereby resulting in a significant color change from yellow to red.[28,29] Thus, colorimetric changes were used to monitor outer membrane integrity. Even at a low concentration (3.9 µM), 5b increased the rate of nitrocefin hydrolysis compared to the spermine-treated or untreated control (FIG. 3a). The behavior was similar to that of the positive control polymyxin-B (PMB) which also produced an increase in nitrocefin hydrolysis. All these data suggest that 5b is able to permeabilize or disrupt the outer membrane of Gram-negative bacteria as no cell lysis was observed.

Figure 3B:
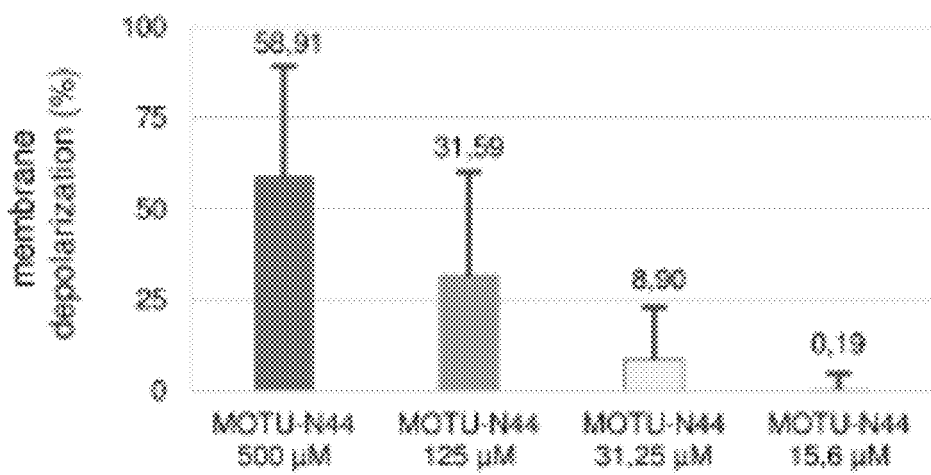
FIG. 3b) Dose-dependent inner-membrane depolarization quantified by the release of $DiSC_3(5)$.

The drug-resistant bacterium EA289 overexpresses the AcrAB-TolC pump (Ref 30), which belongs to the RND efflux pumps and uses the proton gradient across the inner membrane as an energy source. In order to determine if 5b could act as a disruptor of the transmembrane potential, the membrane-potential-sensitive probe $DiSC_3(5)$ was used, which concentrates at the inner membrane and self-quenches its fluorescence.[31] When a compound impairs the membrane potential, the dye is released into the growth medium thus leading to a fluorescence increase. Treatment with 5b resulted in dose-dependent depolarization after 10 min of incubation (FIG. 3b), suggesting disruption of the proton gradient and an ability to affect efflux pumps from the RND family such as AcrAB-TolC.

Figure 3C:
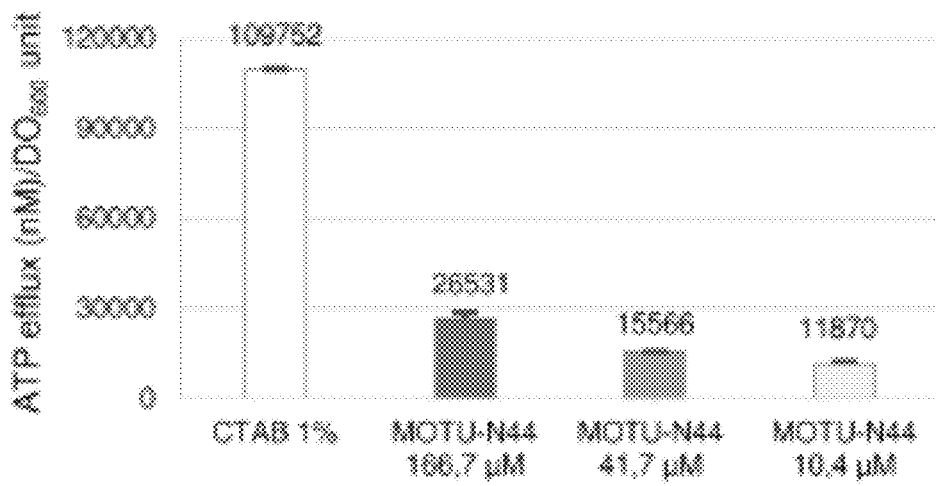
FIG. 3c) Membrane disruption revealed by ATP efflux.

A similar outcome was observed when using a bioluminescence method to determine the release of intracellular ATP. Addition of 5b caused dose-dependent permeabilization (FIG. 3c). Interestingly, 10 µg/mL 5b caused 11% ATP release into the medium after a few seconds, thus, suggesting rapid disruption.

In general, efflux systems employ an energy-dependent mechanism (active transport) to pump out unwanted substances such as toxins, antibiotics, or dyes, through specific efflux pumps.[32] Some efflux systems are drug-specific, whereas others eject multiple drugs, and thus contribute to MDR. Efflux pumps are proteinaceous transporters in the cytoplasmic membrane of bacteria and are active transporters; thus they require a source of chemical energy. Some are primary active transporters that use ATP hydrolysis as a source of energy, whereas in others (secondary active transporters) transport is coupled to an electrochemical potential difference created by pumping protons or sodium ions from or to the outside of the cell. The transport of a known transport substrate can be used to directly monitor the function of efflux pumps, and 5b was thus tested for its ability to inhibit efflux.

Figure 3D:
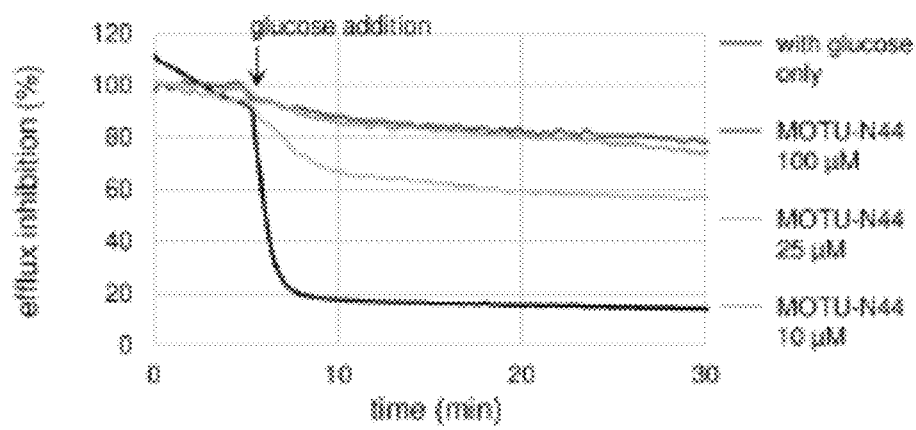
FIG. 3d) Inhibition of glucose-triggered 1,2'-diNA release via efflux pumps.

After loading EA289 bacteria with the dye 1,2'-dinaphthylamine (1,2'-diNA), which is a substrate of the AcrAB-TolC efflux pump,[33] the bacteria fluoresced. Bacteria were then incubated with and without 5b at different concentrations before addition of glucose as an energy source. In the absence of 5b, rapid active transport of more than 80% of the dye was observed (FIG. 3d, black line). When 5b was present, significant dose-dependent inhibition was observed (>80% retention at up to 25 µM 5b; FIG. 3d). These results suggest that 5b inhibits the AcrAB-TolC efflux pump.

Figure 4:
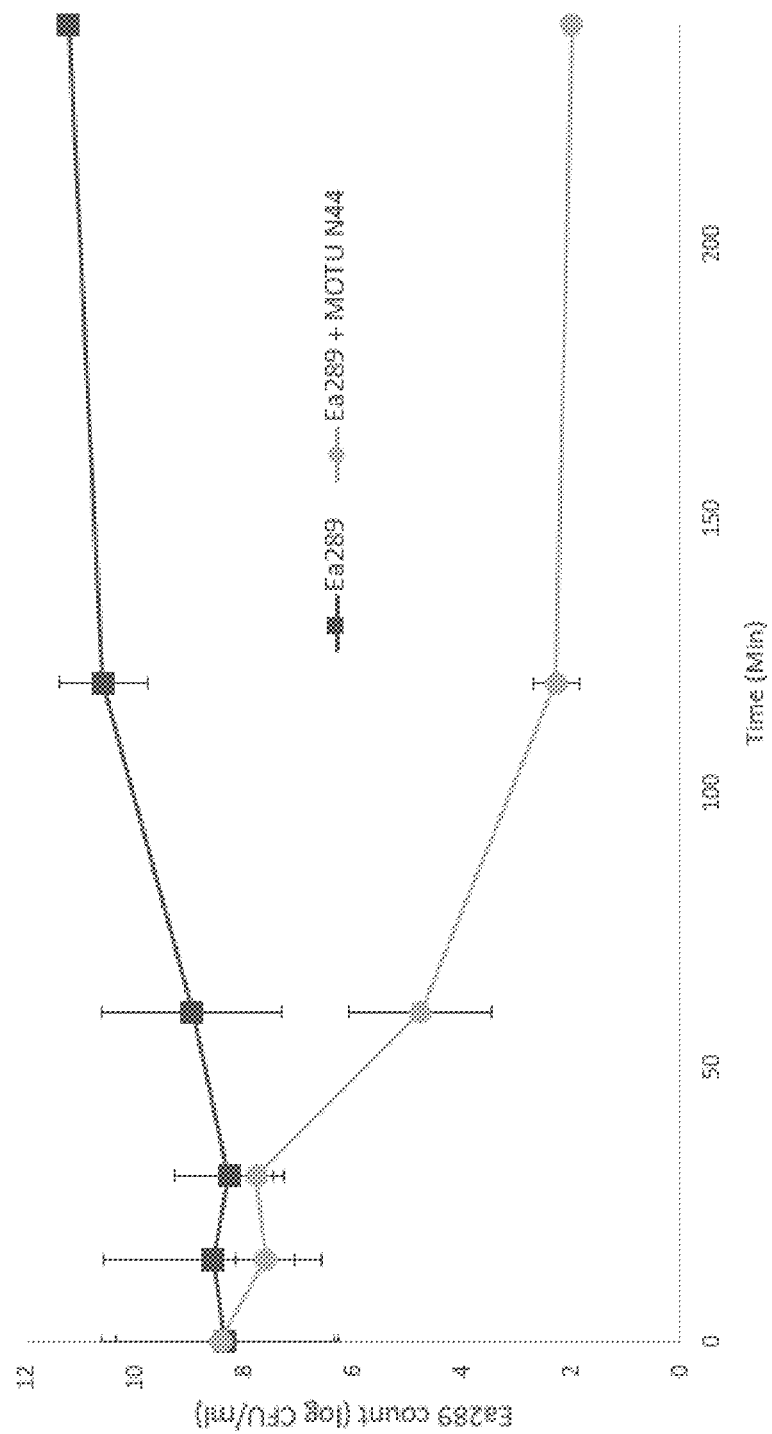
FIG. 4 Time-kill curves of 5b (MOTU-N44, 4×MIC) over 4 h against EA289 bacteria.
Figure 5:
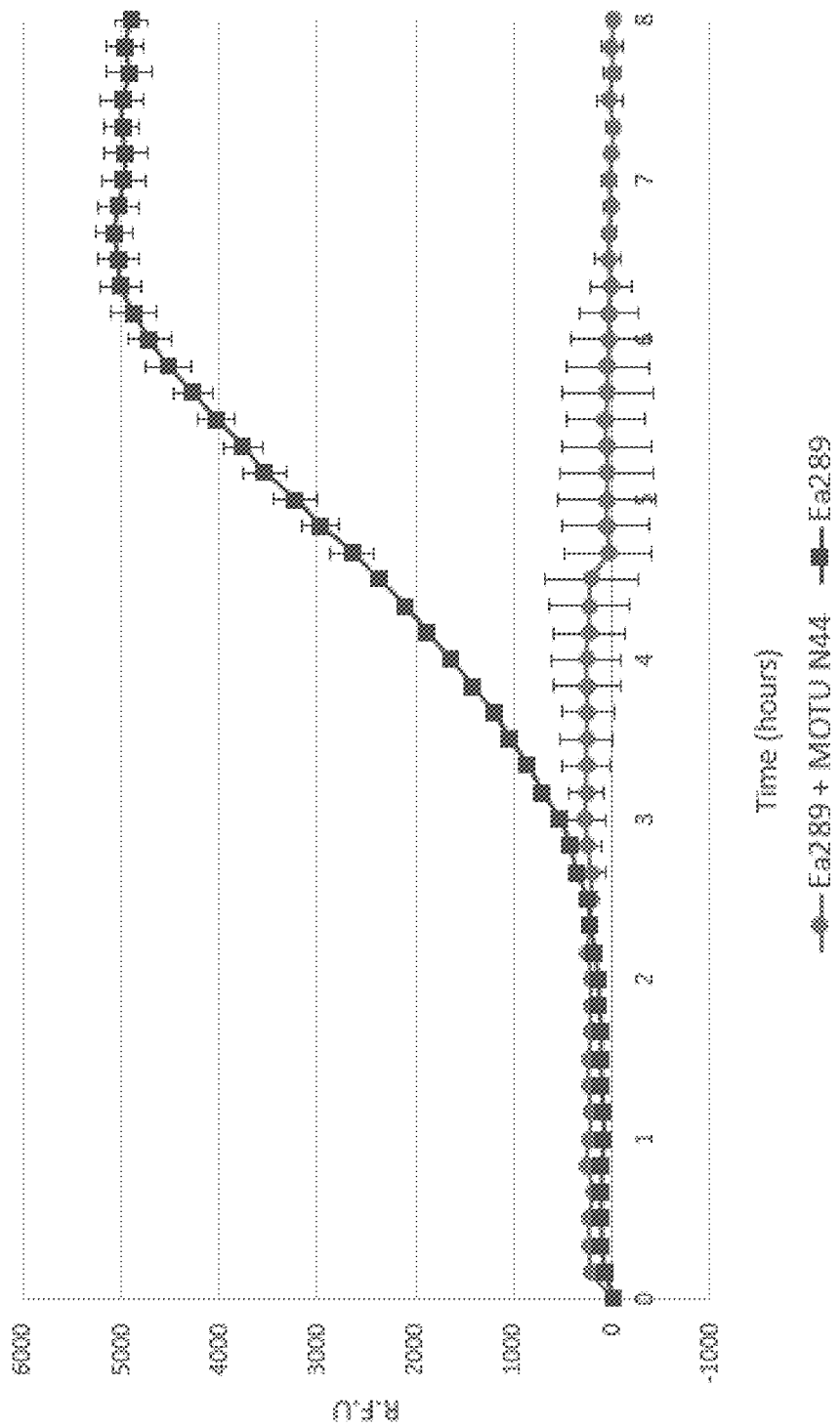
FIG. 5 Cell viability of EA289 in the presence of 5b (MOTU-N44, 4×MIC).
Figure 6:
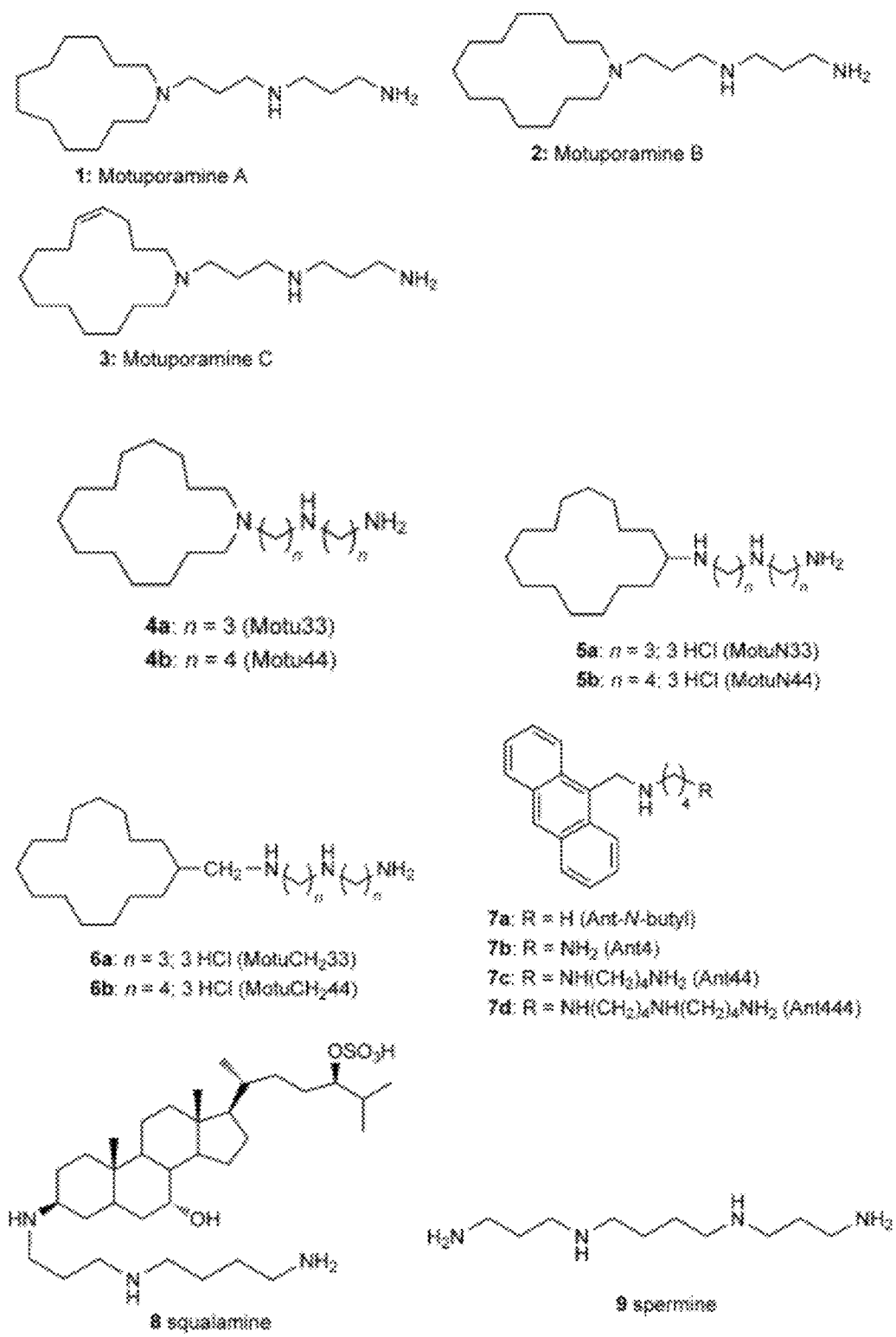
FIG. 6 Schemel Motuporamine compounds 1-6, anthracenyl compounds 7, squalamine 8, and spermine 9.

A time-kill assay (FIG. 4) and a cell viability assay (FIG. 5) were performed in order to evaluate the bactericidal or bacteriostatic behavior of this compound. As shown in FIG.

4, a time kill analysis was performed against the EA289 bacterial strain by using 5b at a four times the MIC: 99.9% death (detection limit) occurred by 2 h.

A cell viability assay (FIG. 5) was performed by monitoring the irreversible reduction of blue resazurin to red resorufin by viable cells. This conversion is an oxidation-reduction indication in cell viability assays and can serve as an aerobic respiration measurement for bacteria.[34] When using 5b at four times the MIC, there was clearly no cell viability.

Thus, the time-kill experiment shows that 5b at four times MIC (200 μM) led to a decrease in live bacteria after 30 min. When the cells were incubated for 60 min at this concentration, the cell viability assay demonstrated total inhibition of respiratory metabolism allowing us to conclude that this decrease in bacterial count correlates highly with cell death.

The real-time assay demonstrated the ability of 5b to inhibit efflux transport to around 60% by using a sub-inhibitory concentration (10 μM, MIC/4). The results from the time-kill assay allow us to state that the cells remain viable in the efflux assay conditions (≤30 min) and that the inhibition of the dye transport is a consequence of a specific action of the compound.

On the other hand, the nitrocefin hydrolysis and membrane depolarization assays suggest that efflux inhibition is probably due to disruption of membrane integrity thereby leading to proton-motive force dissipation. Indeed, the hydrolysis kinetics observed at a low concentration of 5b demonstrated a slight effect on the membrane, thus correlating with the results obtained for the depolarization assay. It was noted that outer-membrane permeation increased with increasing 5b concentration, and this is likely responsible for cell death at high levels. It is also noted that the real-time assays required higher concentrations than those for fixed incubation times to generate a quantifiable signal.

Wang et al recently described a similar action of the substituted diamine, 1,13-bis (((2,2-diphenyl)-1-ethyl)thioureido)-4,10-diazatridecane.[35] This diamine compound was also shown to depolarize the cytoplasmic membrane and provide enhanced permeabilization of the outer bacterial membrane. Further structure—activity relationship studies revealed that the central diamine nitrogens were key to bioactivity. In contrast to the N-substituted systems, the unsubstituted diamines (putrescine and cadaverine) had no antibacterial activity, did not affect membrane permeability, and did not cause membrane rupture. Both of the higher polyamines (spermidine and spermine) were found to be inactive against S. aureus RN4220, P. aeruginosa PAO1 and E. coli ANSI. This, when coupled to our findings, suggests that either mono- or di-substituted polyamine systems can serve as antibacterial agents, whereas the unsubstituted native polyamine systems do not. Taken together, the studies herein also suggest that the presence of hydrophobic N-substituents is key to the ability of these compounds to target bacterial membranes and elicit a bacteriocidal response.

Conclusion

Several polyamine derivatives were investigated for their intrinsic antimicrobial activities against Gram-positive and Gram-negative bacteria. Derivatives 5a and 5b showed excellent activities (MIC 1.56-100 μM). In addition, 5b dramatically affected the antibiotic susceptibility of E. aerogenes, P. aeruginosa, and K. pneumoniae MDR strains. It is believed that changes in the transmembrane electrical potential in E. aerogenes EA289 correlate with permeabilization of the cell membrane by motuporamine derivatives, thereby leading to (or concomitantly facilitating) an altered proton homeostasis. Finally, motuporamine derivatives such as 5b, that are able to disrupt the proton gradient, effectively de-energize the efflux pump and can be considered as efflux-pump inhibitors.

Experimental Section

Bacterial Strains:

Eight bacterial strains were used in this study Institut Pasteur and personal collection. Gram-positive bacteria (S. aureus ATCC25923, S. intermedius 1051997, Enterococcus faecalis ATCC29212) and Gram-negative bacteria (E. coli ATCC28922, P. aeruginosa PAO1, E. aerogenes EA289, a Kan derivative of the MDR clinical isolate Ea27,[30] and K. pneumoniae KPC2 ST258) were stored at M-80° C. in glycerol (15%, v/v). Bacteria were grown in Mueller-Hinton (MH) broth at 37° C.

Antibiotics:

All the antibiotics were purchased from Sigma-Aldrich except for doxycycline which was purchased from TCI Europe (Zwijndrecht, Belgium). All antibiotics were dissolved in water. The susceptibility of bacterial strains to antibiotics and compounds was determined in microplates by the standard broth dilution method, according to the recommendations of the Comité de l'AntibioGramme de la Société Française de Microbiologie (CA-SFM).[36] Briefly, MICs were determined with an inoculum of $10^5$ CFU in of MH broth (200 μL) containing twofold serial dilutions of each drug. MIC was defined as the lowest concentration to completely inhibit growth after incubation for 18h at 37° C. Measurements were repeated in triplicate.

Determination of Antibiotic MIC in the Presence of Compounds:

Briefly, restoring enhancer concentrations were determined with an inoculum of $5\times10^5$ colony forming unit (CFU) in MH broth (200 μL) containing twofold serial dilutions of each derivative and antibiotic (chloramphenicol, doxycycline, cefepime, or erythromycin; 2 μg/mL). The lowest concentration of the polyamine adjuvant that completely inhibited growth after incubation for 18 h at 37° C. was determined. Measurements were repeated in triplicate.

Membrane Depolarization Assays:

Bacteria were grown in MH broth for 24 h at 37° C. and centrifuged (10,000 rpm (3600 G), min, 20° C.). The pellet was washed twice with buffered sucrose (HEPES pH 7.2, 250 mm) and magnesium sulfate (5 mm). The fluorescent dye 3,3'-diethylthiacarbocyanine iodide was added (3 μM) and allowed to penetrate into bacterial membranes by incubation for 1h of at 37° C. Cells were then washed to remove the unbound dye before adding 5b at different concentrations. Fluorescence measurements were performed on a FluoroMax 3 spectrofluorometer (Horiba; slit widths 5/5 nm). The relative corrected fluorescence (RFU) was recorded at 0, 3, 5, 7, 9, 11, 13, 15, 17, 19, and 21 min. Maximum RFU was that recorded with a pure solution of the fluorescent dye in buffer (3 μM).

Nitrocefin Hydrolysis Assay:

Outer membrane permeabilization was measured by using nitrocefin, a chromogenic substrate of periplasmic β-lactamase. MH broth (10 mL) was inoculated with of an overnight culture (0.1 mL) of EA289 and grown at 37° C. to $OD_{600}$=0.5. The remaining steps were performed at room temperature. Cells were recovered by centrifugation (3600G, 20 min) and washed once with potassium phosphate buffer (PPB) (20 mM, pH 7.2) containing $MgCl_2$ (1 mM). After another centrifugation, the pellet was resuspended in PPB (100 μL) and adjusted to $OD_{600}$=0.5. Then, either Polymyxin B (positive control; Sigma-Aldrich) or 5b (50 μL) was added to the cell suspension (100 gm/L) to final concentrations of 0.98-500 μM "2.5, 15, 62.5, and 125 μM".

Nitrocefin (50 μL, 50 μg/mL; Oxoid) was added, and its hydrolysis was monitored spectrophotometrically by measuring the increase in absorbance at 490 nm. Assays were performed in 96-well plates with an M200 Pro spectrophotometer (Tecan).

Glucose-Triggered 1,2'-diNA Efflux Assays:

Bacteria were grown to stationary phase, collected by centrifugation, and resuspended to $OD_{600}$=0.25 in potassium phosphate buffer (20 mM, pH 7.2) supplemented with carbonyl cyanide m-chlorophenyl hydrazone (CCCP, 5 μM; Sigma-Aldrich), and incubated overnight with 1,2'-dinaphthylamine (1,2'-diNA, 32 μM; Sigma-Aldrich) at 37° C. Before addition of compound 5b (100 μM), the cells were washed with phosphate buffer. Glucose (50 mm) was added after 300 s to initiate bacterial energization. Release of membrane-incorporated 1,2'-diNA was followed by monitoring the fluorescence ($\lambda_{ex}$=370 nm; $\lambda_{em}$=420 nm) every 30 s at 37° C. in an Infinite M200 Pro plate reader (Tecan). Assays were performed in 96-well plates (half area, black with solid bottom, 100 μL per well; Greiner Bio-One).

Measurement of ATP Efflux:

Squalamine were prepared in doubly distilled water at different concentrations. A suspension of growing S. aureus or E. aerogenes (EA289) in MH broth was incubated at 37° C. The suspension (90 μL) was added to squalamine solution (10 μL, synthesized in lab according to reported procedures), and the mixture was vortexed for 1 s. Luciferin-luciferase reagent (Yelen, France; 50 μL) was immediately added, and luminescence was quantified with an Infinite M200 microplate reader (Tecan) for 5 s. ATP concentration was quantified by ATP concentration was quantified by addition of a known amount of ATP (1 μM). A similar procedure was performed for spermine (100 μg/mL) and for 5b (200 μM, i.e., 4×MIC).

Time-Killing Assay:

Mid-log phase cultures of EA289 with an inoculum of $10^7$ CFU/mL were incubated with 5b (4×MIC, 200 μM) at 37° C. with 160 rpm shaking. Bacterial counts were performed after 0, 15, 30, 90, 120 and 240 min by spreading appropriate dilutions on MH agar plates (detection limit $10^2$ colony forming unit (CFU)/mL). The plates were incubated overnight at 37° C. before colonies were counted. The curves from two independent experiments were averaged and expressed as logarithms (mean+/−standard error).

Cell Viability Assay:

An overnight culture of EA289 was diluted 100-fold into MHII broth. An inoculum of $10^7$ CFU/mL was incubated in the presence or absence of 5b (4×MIC, 200 μM) for 1 h at 37° C. with shaking at 160 rpm. The fluorescence of the cell suspension was monitored after addition of CellTiter-Blue reagent (10%, v/v; Promega). Measurements were performed by using a 96-well Greiner film-bottom black microplate (Greiner Bio-One) and an Infinite M200 microplate reader (Tecan; $<GI>_{ex}$=568 nm and $<GI>_{em}$=660 nm). The curves from two independent experiments were combined (mean+/−standard error).

Synthesis of Compounds 4-7:

The synthesis of 4-7 was previously reported.[15,637-41]

Example 2: Synthetic Procedures and Characterization

General Synthesis Schemes

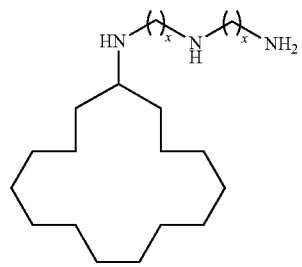

8a: x = 3; 3HCl (MotuN33)
8b: x = 4; 3HCl (MotuN44)

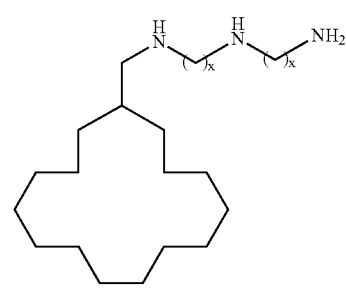

9a: x = 3; 3HCl (MotuCH$_2$33)
9b: x = 4; 3HCl (MotuCH$_2$44)

Synthesized Motuporamine Derivatives 8-9

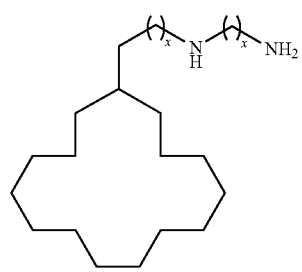

x = 3; 3HCl (MotuCH$_2$CH$_2$33)

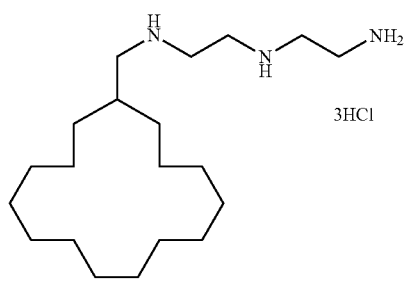

11a

3HCl

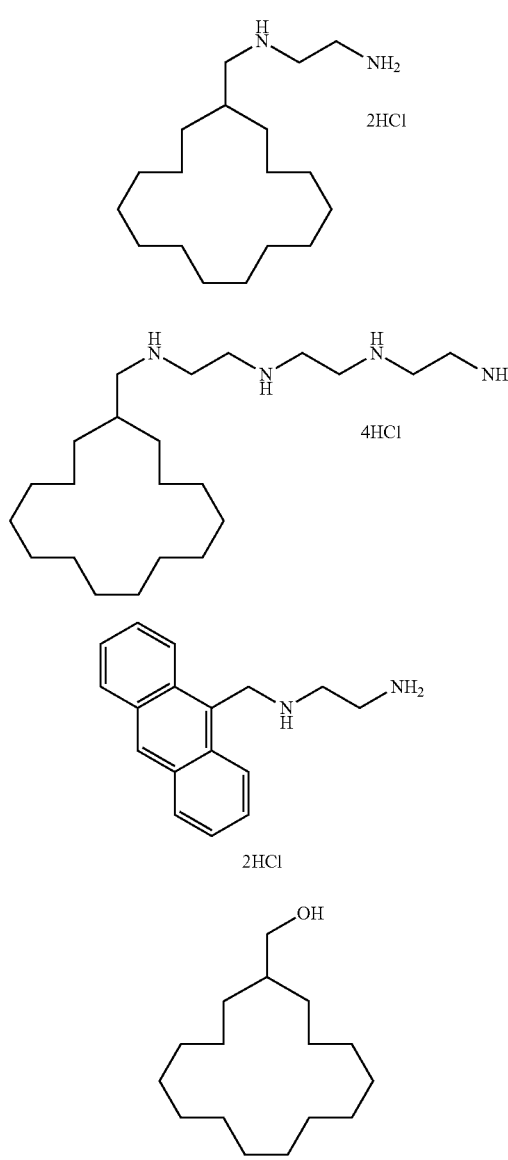

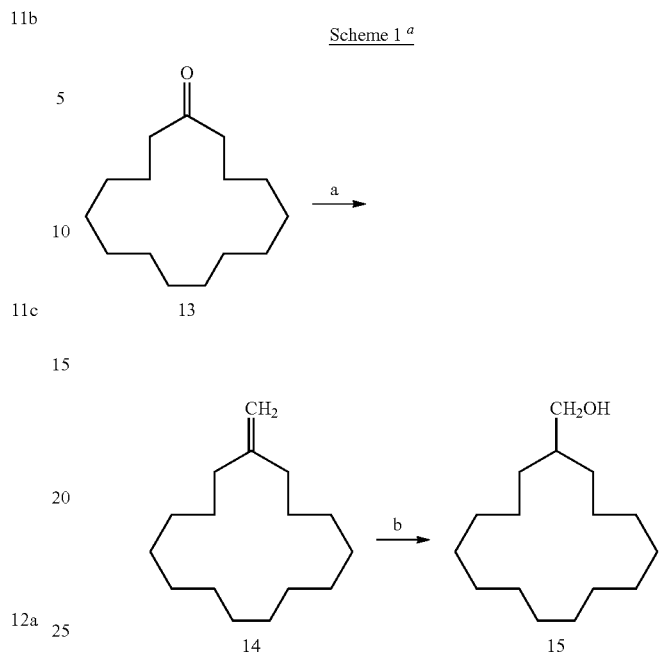

Scheme 1[a]

[a] Reagents: a) MePPh₃I, BuLi; b) BH₃/THF

The alcohol 15 was converted into a good leaving group (by conversion to its mesylate 16) using methane sulfonyl chloride/TEA in DCM in good yields. Mesylate 16 was then converted to nitrile 17 using 18-crown-6 ether and KCN with a yield of 87%. The resultant alkylated nitrile was then reduced to primary amine 18 using lithium aluminum hydride in THF with a 49% yield. Attempts were made to generate the amine on the motuporamine ring with two and three methylene spacers. Synthesis of the two methylene spacer amine 18a was successful while the three spacer amine 18b was problematic due to low yields of its corresponding nitrile 17b (<11%).

New Ethylene Amine motifs based on MotuCH₂33 (9a) and model systems 12a and 15 Compound 10 was generated via a multistep synthetic process from alcohol 15. As shown in Scheme 1, Muth et al demonstrated that it was possible to convert commercially available ketone 13 to its corresponding alkene 14 through a Wittig reagent[5]. The alkene could then undergo hydroboration oxidation to alcohol 15. From alcohol 15 a number of synthetic routes were attempted to use the alcohol as a platform to create an electrophile or a nucleophile. The synthesis of extended motifs on the motuporamines had been attempted by Muth et al by conversion of alcohol 15 to its corresponding aldehyde resulting in low yields and an impure product.[5] While extended compounds 9a and 9b were made from the aldehyde, other chemistries were investigated in an attempt to improve the yields on extended motuporamine structures.

Therefore it was attempted to convert the alcohol to an extended primary amine 18 which could behave as a nucleophile to attack an electrophilic polyamine scaffold, as shown in Schemes 2 and 3.

Scheme 2[a]

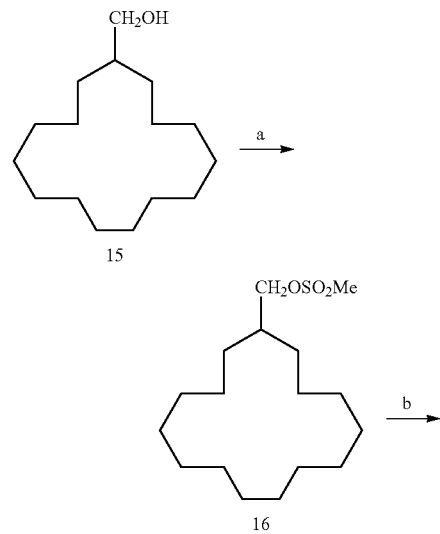

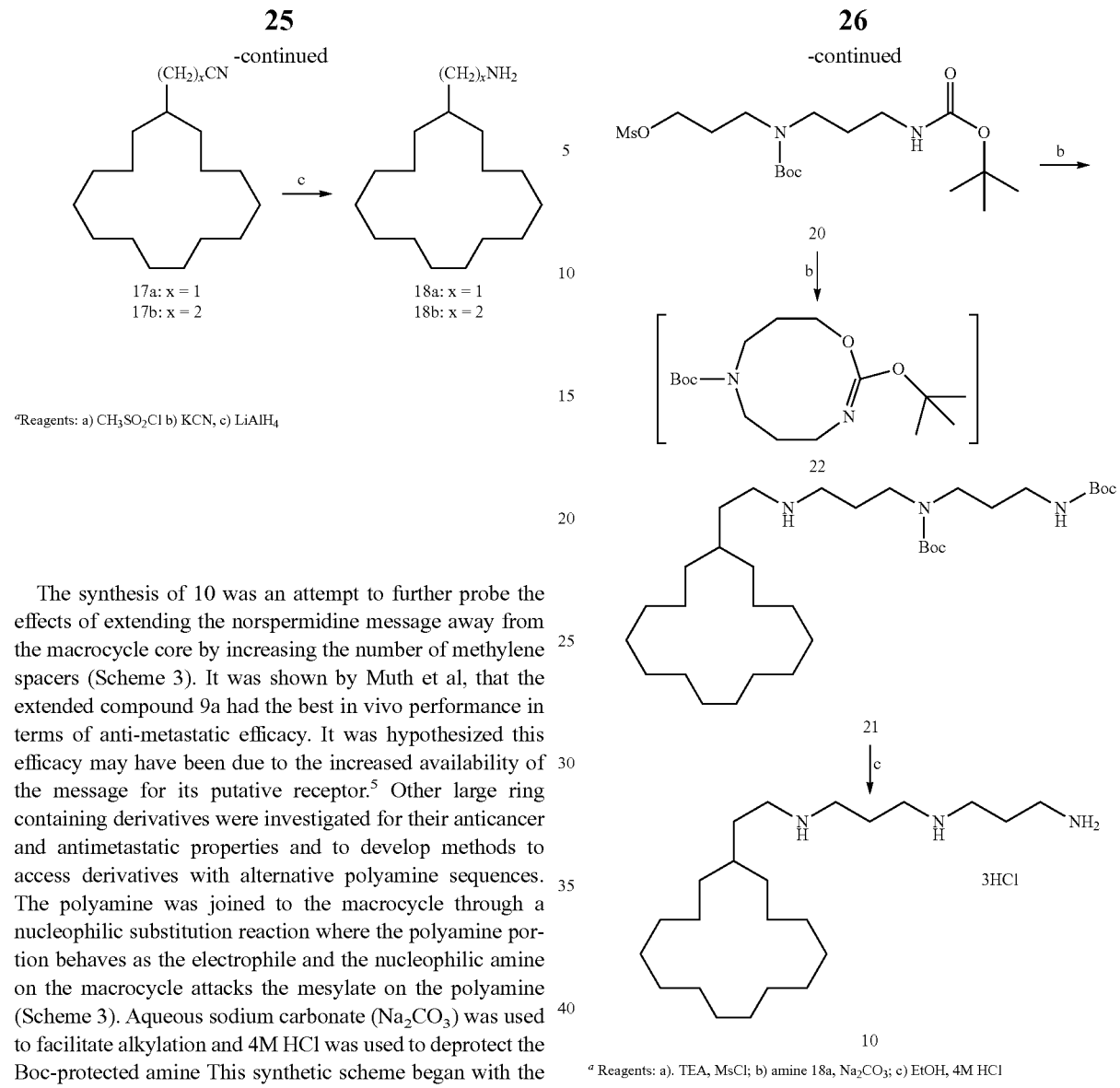

The synthesis of 10 was an attempt to further probe the effects of extending the norspermidine message away from the macrocycle core by increasing the number of methylene spacers (Scheme 3). It was shown by Muth et al, that the extended compound 9a had the best in vivo performance in terms of anti-metastatic efficacy. It was hypothesized this efficacy may have been due to the increased availability of the message for its putative receptor.[5] Other large ring containing derivatives were investigated for their anticancer and antimetastatic properties and to develop methods to access derivatives with alternative polyamine sequences. The polyamine was joined to the macrocycle through a nucleophilic substitution reaction where the polyamine portion behaves as the electrophile and the nucleophilic amine on the macrocycle attacks the mesylate on the polyamine (Scheme 3). Aqueous sodium carbonate ($Na_2CO_3$) was used to facilitate alkylation and 4M HCl was used to deprotect the Boc-protected amine This synthetic scheme began with the conversion of the Boc-protected polyamine 19 to its corresponding mesylate 20 in 80% yield. The N-alkylation of mesylate 20 with amine 18 was performed in the presence of $Na_2CO_3$ in DCM and resulted in poor yield of 20%. As this step also required the use of amine 18, a compound that was generated through a long synthetic method and also resulted in low yields, the scheme was less than satisfactory. The low yields in the synthesis of 21 in particular was attributed to the facile formation of a self-cyclized byproduct 22 where (due to the low reactivity of the macrocyclic amine 18) the terminal carbamate group of 20 was observed to react with and displace the appended mesylate group to form byproduct 22, thus, lowering the amount of 20 available to react.

Scheme 3[a]

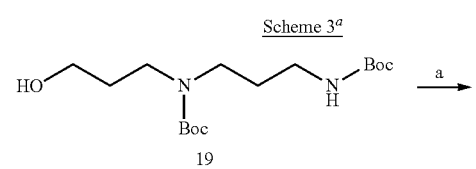

In an attempt to maximize yields and minimize the formation of undesirable side products, a regioselective protection of specific nitrogen centers was performed on the free base of triethylene tetramine tetrahydrochloride 24b and tetraethylenepentamine pentahydrochloride 24c. The general strategy was to cap all the free secondary amine centers on the polyamine chain as carbamates containing t-butoxycarbonyl (Boc) groups. Failure to cap these potential nucleophilic centers would result in undesired non-linear, branched byproducts. Selective protection was performed by formation of an imine on the primary amine of the free base form of the polyamine using salicylaldehyde (Scheme 5).[18] Salicylaldehyde will selectively protect primary amines but leave the secondary amines untouched and therefore the secondary amines are subject to protective Bocylation using di-tert-butyl dicarbonate.

After the Boc protection of the secondary amine and remaining primary amine centers was complete, cleavage of the imine was performed with methoxyamine under acid-free conditions to maintain the fidelity of Boc protection.[19] Deprotection of the salicylimine afforded a polyamine chain with one available primary amine as a reactive center for selective alkylation with the macrocycle mesylate 16.

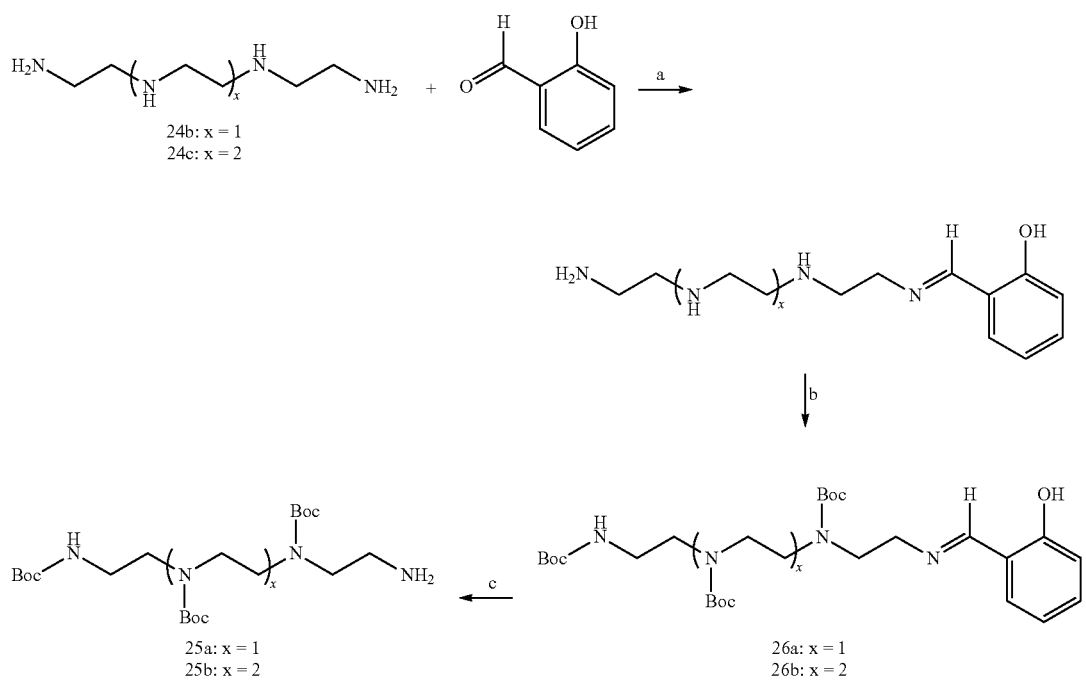

<sup>a</sup>Reagents: a) NaOH; b) di-tert-butyl dicarbonate; c) MeONH$_2$

This route in Scheme 5 provided the required Boc-protected polyamines for coupling to the large macrocycle.

The other systems (11a-c) were made via Schemes 6 and 7 below:

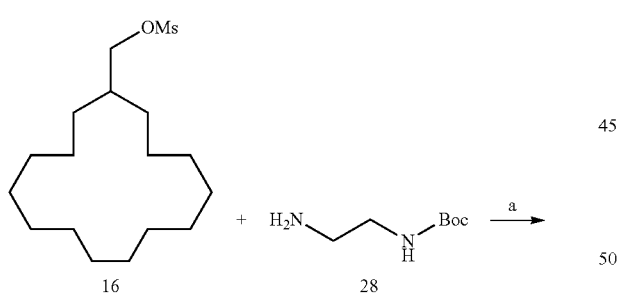

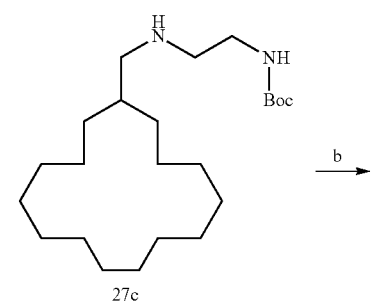

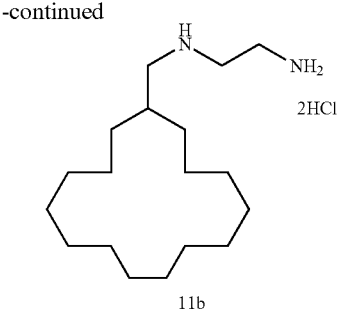

<sup>a</sup>Reagents: a) CH$_3$CN, K$_2$CO$_3$ b) 4M HCl, EtOH

Mono N-Boc diamine 28 was available commercially (Sigma Aldrich) and was the only Boc protected ethylene amine motif to be used successfully in forming the desired motuporamine structure. The Boc protected polyamine 28 was heated at 50° C. overnight and then for 5 days at reflux (80° C.). The reaction rate was shown to increase after 48 h when the volume of the solvent (CH$_3$CN) was reduced. The product 27c was able to be separated by column chromatography (7% MeOH/DCM R$_f$ of 27c: 0.4) from a cyclized urea byproduct that was present in large quantities for a total yield of 27c of 53% (Scheme 6). Subsequent removal of the Boc group with acid provided the desired adduct 11b in high yield but at a disappointing 10% overall yield from 16.

Another route to the desired target using unprotected polyamines was investigated.

Scheme 7[a]

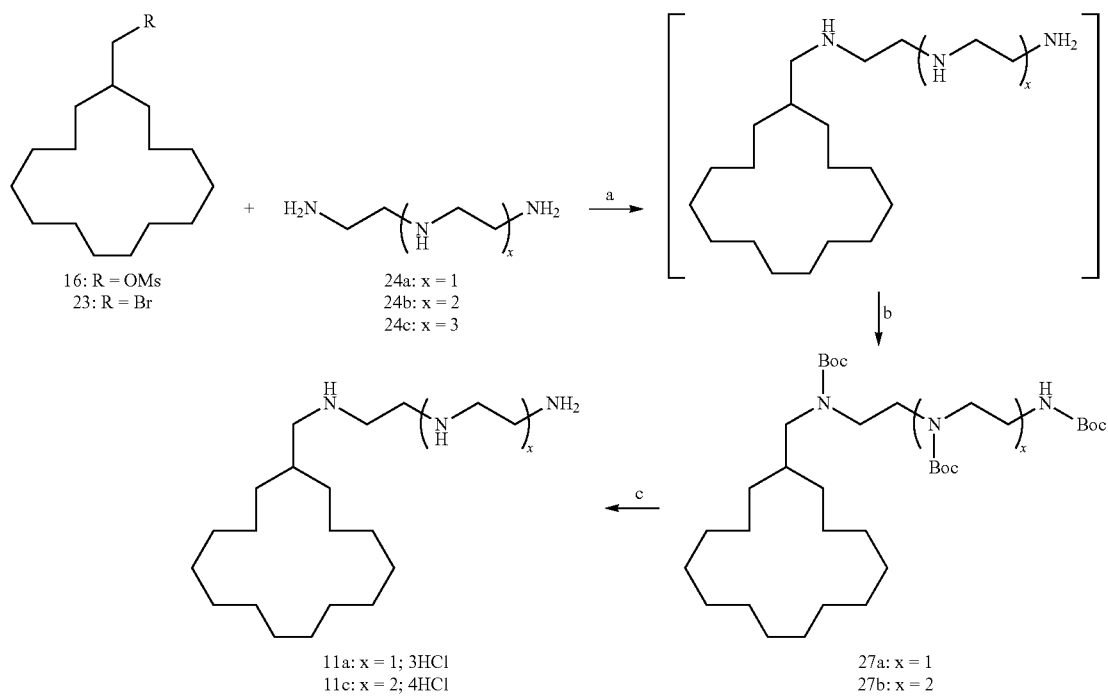

[a]Reagents: a) CH$_3$CN, K$_2$CO$_3$; b) di-tert-butyl dibicarbonate; c) EtOH, 4M HCl As Boc protected polyamines appeared to have hindered reactivity due to their Boc groups and displaced their own t-butyl groups to form cyclic ureas in favor of reacting with the mesylate 16, a 'naked polyamine' approach was attempted with the free base of 24a,b,c as shown in Scheme 7. This approach was not initially attempted due to the probability of the secondary internal amines reacting with the mesylate and creating tertiary branched motuporamine structures instead of the desired secondary amine containing linear motuporamine motifs. Nevertheless, this 'naked polyamine' approach avoided the possibility of the polyamine portion reacting with its own Boc group prior to alkylation. Indeed, the reaction was much more facile without the bulky Boc substituents crowding the primary amine reaction center. This approach was successful with 24a and 24b while 24c was less productive. In the production of 11a, triamine 24a was reacted with bromide 23 while in the production of 11c, tetraamine 24b was reacted with mesyl 16. With both 24a and 24b the respective alkylations were performed in CH$_3$CN and showed complete disappearance of each starting material after 72 h. Workups were performed with 0.1M NaOH and DCM to remove the salts and in the case of 24b, the displaced methanesulfonate. These provided the expected mixture of secondary and tertiary alkylated products. These were separated by installing Boc groups at every secondary and primary amine center via bocylation. Since the tertiary amine would not be N-bocylated, the byproduct retained its amine functional group whereas the desired product was converted to a polycarbamate motif. This change in functional group allowed for easy separation by column chromatography of the undesired tertiary amine byproduct (which had one less Boc group and was chemically distinct) and the desired motuporamine motif. Using this approach, a 25% yield was achieved for both products.

The use of the pentamine 24c with this method achieved a different result. The free base of pentamine 24c was prepared and mesylate 16 was added in CH$_3$CN and refluxed for 72 h and monitored by NMR (similar to 24a sequence in Scheme 7). The mixture was then per-bocylated and separated by column chromatography (1% NH$_4$OH/4.5% MeOH/DCM, R$_f$ of suspected product 0.4 and an additional unknown spot at R$_f$ 0.47). Multiple attempts to separate the product failed and ultimately the final product was both unresolvable from its upper spot and appeared to be the cyclized byproduct by NMR. The crude weight also suggested it was a significantly less productive reaction due to the low conversion of starting material at high temperatures and over a long period of time. Therefore, there were clear limitations to using this approach. Nevertheless, these synthetic routes provided materials for testing in biological systems.

Lastly, an anthryl control compound 12a was made for comparisons in Scheme 8.

Scheme 5[a]

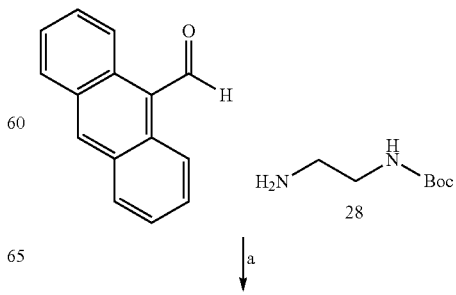

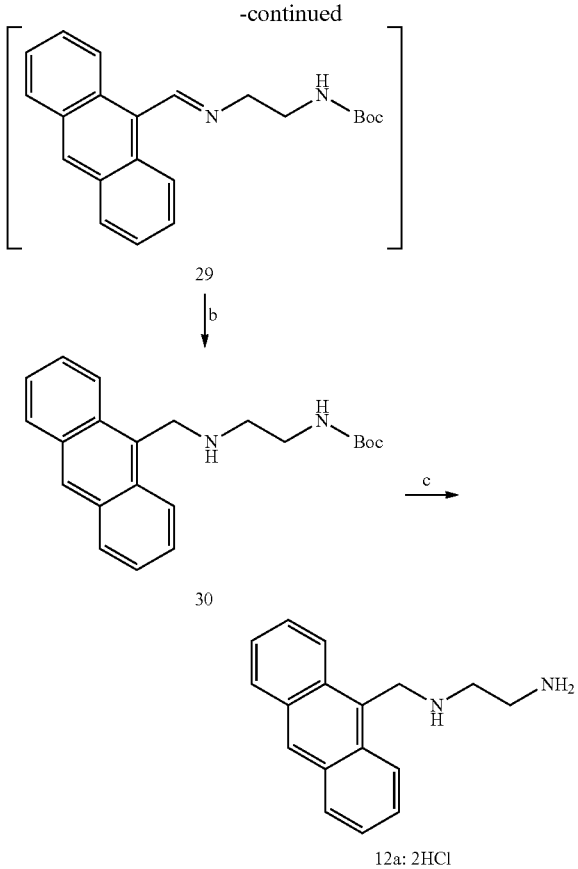

*Reagents: a) 25% MeOH/DCM; b) NaBH₄; c) EtOH, 4M HCl

The synthetic scheme for $N^1$-Anthracen-9-ylmethyl-ethane-1,2-diamine 12a is shown in Scheme 8 and was based on prior work established in Gardner et al[21] to synthesize Ant44 (12b). In the synthesis of 12a, the ethylene amine motif was joined via reductive amination to the commercially available 9-anthraldehyde (Sigma Aldrich) which resulted in 75% yield over 3 steps via the intermediate imine 29.

Detailed Synthesis Procedures

Synthesis of Compounds 4-7:

The synthesis of 4-7 was previously reported.[15,37-41]

N-(3-Amino-propyl)-N'-(2-cyclopentadecylethyl)-propane-1,3-diamine 10

Compound 21 was dissolved in 200 proof EtOH (1 mL) and slowly added dropwise to 4M HCl (1.56 mL) at 0° C. After the addition was complete, the solution was brought to rt and stirred for 24 h. It was then concentrated under reduced pressure to yield the product 10. (20 mg, 0.042 mmol, 74% yield). 10: $^1$H NMR (D₂O): δ 3.10 (m, 10H, $J^3_{H-H}$=6.1 Hz), 2.09 (m, 4H), 1.58 (m, 2H), 1.45 (m, 1H), 1.29 (s, 28H); $^{13}$C NMR (CDCl₃): δ 45.89, 43.89, 36.80, 33.65, 33.49, 31.28, 30.92, 30.27, 28.69, 28.07, 27.44, 27.41, 26.46, 25.77, 25.60, 23.98, 23.48. HRMS calc for $C_{23}H_{49}N_3$ (M+H) 367.392, found 367.3926. Compound 10 was 93% pure by HPLC analysis [UV detection at 210 nm showed a major peak eluted (~5 min) on a $C_{18}$ column using 60% acetonitrile/an aqueous heptane sulfonate buffer at pH 3.8 with a flowrate of 1 mL/min].

N-(2-Amino-ethyl)-N'-cyclopentadecylmethyl-ethane-1,2-diamine 11a.

Compound 27a (96 mg, 0.153 mmol) was then dissolved in EtOH (3 mL) and 4M HCl in EtOH (3 mL) while stirring overnight at rt. The solvent was then removed under reduced pressure to give a white solid 11a (60 mg, 0.138 mmol, 90% yield). 11a. $^1$H NMR (D₂O): δ 3.45 (m, 8H), 3.02 (br s, 2H), 1.83 (br s, 1H), 1.32 (br s, 28H); $^{13}$C NMR (D₂O): δ 55.57, 47.12, 46.04, 37.92, 36.74, 31.84, 29.29, 28.94, 28.88, 28.55, 26.09. HRMS for $C_{20}H_{43}N_3$ (M+H) Theory: 325.3439 Found: 325.3457. Anal Calcd $C_{20}H_{46}Cl_3N_3$ 0.56; H₂O: Theory: C, 53.98, H, 10.67, N, 9.44 . Found: C, 54.38, H, 10.68 N, 9.05.

N1-Cyclopentadecylmethyl-ethane-1,2-diamine 11b

Compound 27c (61 mg, 0.16 mmol) was dissolved in EtOH (1 mL) and 4M HCl/EtOH (1 mL) was added dropwise and stirred at rt overnight. The solvent was then removed under reduced pressure for a white solid 11b (50 mg, 0.157 mmol, 98% yield). 11b: $^1$H NMR (D₂O): δ 3.39 (br s, 4H), 3.01 (br s, 2H), 1.82 (br s, 1H), 1.33 (br s, 28H); $^{13}$C NMR (D₂O): δ 55.48, 47.30, 37.97, 36.73, 31.84, 29.29, 28.90, 28.56, 26.09. Anal Calcd for $C_{18}H_{40}Cl_2N_2$ 0.05 H₂O: theory C, 60.83, H, 11.34, N, 7.88; found C, 61.12, H, 11.44, N, 7.72.

N-[2-(2-Amino-ethylamino)-ethyl]-N'-cyclopentadecylmethyl-ethane-1,2-diamine 11c Removal of the Boc groups of 27b was performed in 4M HCl/EtOH by first dissolving the product in 200 proof EtOH (5 mL) which required sonication. 4M HCl in EtOH (5 mL) was then added dropwise while stirring. Reaction proceeded overnight, the solvent was then removed under reduced pressure for a weight of the final product, a white solid, 11c (252 mg, 0.49 mmol, 98% yield). 11c: $^1$H NMR (D₂O): δ 3.51 (m, 12H), 3.04 (br s, 2H), 1.86 (br s, 1H), 1.33 (s, 28H); $^{13}$C NMR (D₂O): δ 55.43, 47.07, 46.44, 46.15, 38.03, 36.64, 31.79, 30.50, 29.42, 29.05, 28.80, 26.08. HRMS $C_{22}H_{48}N_4$ (M+H) Theory: 368.3878, Found: 368.3879; Anal Calcd $C_{22}H_{52}Cl_4N_4$ Theory: C, 51.36, H, 10.19, N, 10.89 Found: C, 51.35, H, 10.46, N, 10.62.

N1-Anthracen-9-ylmethyl-ethane-1,2-diamine 12a

To a stirred solution of monoBoc diamine 28 (268 mg, 1.67 mmol) in 25% methanol/DCM (10 mL) was added a solution of 9-anthraldehyde (289 mg, 1.40 mmol) in 5 mL of 25% methanol/DCM under N₂. The solution was allowed to stir at rt overnight until imine formation was complete (monitored by $^1$H NMR). The solvent was removed in vacuo and the crude imine 29 was re-dissolved in 50% Methanol/DCM and cooled to 0° C. NaBH₄ (167 mg, 4.28 mmol) was added and the mixture was stirred at rt overnight. The solvents were removed under vacuum, and the residue was redissolved in DCM and washed with saturated Na₂CO₃. The organic layer was separated, dried over anhydrous Na₂SO₄, filtered and concentrated to give a solid (521 mg crude) which was purified by 5% MeOH/CHCl₃ to yield 412 mg (1.18 mmol) of the desired adduct 30 (80% yield). Debocylation with 2 mL of ethanol and 2 mL of 4M HCl gave the product (340 mg, 1.05 mmol, 89% yield) for an overall yield of 75%. 12a: $^1$H NMR (D₂O): δ 8.40 (s, 1H), 8.05 (m, 2H), 7.63 (m, 2H), 7.53 (m, 2H), 4.95 (s, 2H), 3.55 (m, 2H), 3.35 (m, 2H); $^{13}$C NMR (25% $d_6$-DMSO in D₂O): δ 133.4, 132.8, 131.9, 130.3, 128.3, 125.4, 124.3, 47.3, 46.0, 38.26

Methylenecyclopentadecane 14

To a stirred solution of methyltriphenyl phosphonium iodide (27.17g, 66.9 mmol) in freshly distilled anhydrous THF (300 mL) was added n-Butyl Lithium (n-BuLi, 66.9 mmol, 1.6M in hexanes) dropwise under $N_2$ via syringe at 0° C. The solution immediately turned a dark brown-reddish color and the contents of the solution dissolved. Prior to addition of n-BuLi, attempts were made to dissolve the MePh$_3$PI in THF but dissolution only occurred upon n-BuLi addition. After the Wittig reagent had formed (20 minutes), ketone 13 (5 g, 22.3 mmol) was added in a minimal amount of THF followed by an additional 5.0 g of ketone (for a total of 44.6 mmol). The reaction was allowed to warm to room temperature and stir overnight. The reaction was monitored for the presence of ketone 13 by TLC (5% ethyl acetate/hexane with KMnO$_4$ staining and by $^1$H NMR). Additional butyl lithium (10 mL) was added under the same conditions after 48 h after NMR showed only 45% conversion. An additional 10 mL of BuLi was added at the 72 h time point. After 96 h the reaction was worked up by quenching excess BuLi at 0° C. with deionized water. The contents were then filtered with minimal amounts of white solid present and the THF was removed under reduced pressure revealing a biphasic red-yellow mixture. The mixture was redissolved in DCM, the layers were separated, the aqueous layer was washed with DCM (3x) and then the DCM was removed to yield a biphasic crude with a red solid and a yellow oil (30.9 g). The red solid was assumed to be the triphenyl phosphonium oxide. The residue was then washed 3x with hexanes and then the solvent was removed to reveal a yellow non-viscous oil (10.7 g). The crude mixture was then separated by column chromatography (10% DCM, hexanes) to yield alkene 14 as a colorless oil. (4.9 g, 22.4 mmol, 50% yield).

Cyclopentadecylmethanol 15.[5]

Alkene 14 (4.97 g, 22.4 mmol) was added dropwise at 0° C. to a BH$_3$-THF solution (67 mmol, 5.7 g, 14.9 mL). The reaction was stirred for 1 h at 0° C. and then allowed to warm to room temp and stir for 2 h. The reaction progress was monitored for disappearance of the alkene and then the excess BH$_3$ was quenched with deionized water (31 mL) after pre-cooling the mixture to 0° C. 3M NaOH (31 mL) followed by 30% H$_2$O$_2$ (31 mL) was added over the course of 1 h at 0° C. for the oxidation step in the workup and the reaction was stirred overnight. K$_2$CO$_3$ (300 mg: 2.17 mmol) was added and then the THF was removed under reduced pressure. DCM was then added, the layers were separated, and the aqueous layer was extracted three times with DCM, the organic layers were pooled, dried over anhydrous Na$_2$SO$_4$, filtered and concentrated to give a viscous light yellow oil (5.2 g). TLC (20% Hexanes/DCM, visualization with phosphomolybdic acid, $R_f$ 0.3). Column (100% DCM) was run to separate the crude for a clear oil (3.9 g, 16.2 mmol, 73% yield). $^1$H NMR analysis matched the literature spectrum for this compound.[5]

Methanesulfonic Acid Cyclopentadecylmethyl Ester 16

Alcohol 15 (998 mg, 4.15 mmol) was added to TEA (643 µL, 4.58 mmol) in DCM. Methanesulfonyl chloride was then dispensed by syringe (355 µL, 4.58 mmol) at 0° C. and stirred overnight at rt. The reaction was monitored by TLC (100% CH$_2$Cl$_2$, $R_f$ mesylate 16: 0.63; $R_f$ alcohol 15: 0.37) and then quenched with 1M NaOH (2 mL). The organic phase was washed three times with 1M NaOH (5 mL), then separated, dried over anhydrous Na$_2$SO$_4$, filtered and concentrated to give the mesylate 16 as a yellow oil (1.12 g, 3.52 mmol, 85% yield). $^1$H NMR (CDCl$_3$): δ 4.15 (d, 2H, $J^3_{H-H}$6.1 Hz), 3.0 (s, 3H), 1.34 (br s, 29H).

Cyclopentadecyl-Acetonitrile 17

KCN (3.09 g, 47.6 mmol), 18-crown-6 ether (145 mg, 0.48 mmol), and dry CH$_3$CN (48 mL) were added to mesylate 16 (1.69 g, 5.29 mmol) and the reaction was refluxed overnight. The reaction was monitored by TLC (70% Hexanes/CH$_2$Cl$_2$, $R_f$=0.28) and then volatiles were removed, the residue was redissolved in DCM and washed with water. The layers were separated, the organic layer was dried over anhydrous Na$_2$SO$_4$, filtered and concentrated to give a yellow crude oil (1.29 g, 5.17 mmol) which was then purified by column chromatography (70% Hexanes/CH$_2$Cl$_2$) and concentrated under reduced pressure and subjected to high vacuum yielding a colorless oil (0.92 g, 3.69 mmol, 82% yield, 91% conversion). Mesylate 16 was recovered as a white crystalline solid (0.15 g, 0.47 mmol, 9% recovery) in (50% Hexanes/CH$_2$Cl$_2$, $R_f$ 0.3). $^1$H NMR: δ 2.30 (d, 2H, $J^3_{H-H}$6.6 Hz), 1.80 (m, 1H), 1.34 (br s, 28H). $^{13}$C NMR: δ 119.2, 33.7, 31.8, 27.1, 26.8, 26.7, 26.6, 26.5, 24.3, 22.9. HRMS for C$_{17}$H$_{31}$N (M+H): 250.2535, found 250.2527. Anal. C$_{17}$H$_{31}$N: Theory: C, 81.86, H, 12.53, N, 5.62 Found: 82.04, 12.63, N, 5.51.

2-Cyclopentadecyl-Ethylamine 18

Nitrile 17 (412 mg, 1.64 mmol) was dissolved in dry THF (5 mL, 55.5 mmol) and added dropwise to a stirred solution of LiAlH$_4$ (207 mg, 5.46 mmol) in THF (5 mL) at 0° C. The reaction was then warmed to rt and refluxed overnight. The reaction was monitored for the disappearance of the nitrile with TLC (1% NH$_4$OH/15% MeOH/CH$_2$Cl$_2$, $R_f$ Amine=0.28, $R_f$ Nitrile=0.55). After disappearance of the starting material was confirmed by TLC, the reaction mixture was concentrated and redissolved in DCM. The organic phase was washed with a solution of water (0.9 mL) and 5M NaOH (0.15 mL), and the organic layer was separated, dried over anhydrous Na$_2$SO$_4$, filtered and concentrated under reduced pressure to yield a colorless oil. Column chromatography (85% CH$_2$Cl$_2$, 15% Methanol, 1 drop NH$_4$OH) provided amine 18 (203 mg, 0.80 mmol, 49% yield). 18: $^1$H NMR: δ 2.72 (m, 2H), 1.41 (m, 4H), 1.34 (m, 28H); $^{13}$C NMR: δ 40.00, 38.86, 34.17, 32.42, 27.58, 26.93, 26.59; HRMS for C$_{17}$H$_{35}$N (M+H): 253.2789, found 253.277; Anal. C$_{17}$H$_{35}$N, 0.2 H$_2$O Theory: C, 79.43, H, 13.88, N, 5.45 Found: C, 79.24, H, 13.94, N, 5.37.

Methanesulfonic acid 3-[tert-butoxycarbonyl-(3-tert-butoxycarboynlamino-propyl)-amino]-propyl ester 20

DiBoc 33 triamine alcohol 19[10b] (3-tert-Butoxycarbonylaminopropyl)-(3-hydroxypropyl) carbamic acid tert-butyl ester, 100 mg, 0.3 mmol) was added to TEA (127 µL, 0.9 mmol) and CH$_2$Cl$_2$ (3 mL). Methane sulfonyl chloride (34.9 µL, 0.45 mmol) was added dropwise at 0° C. via syringe under a nitrogen atmosphere. Once the addition was complete, the syringe was rinsed with CH$_2$Cl$_2$ (0.6 mL). Reaction progress monitored by TLC (5% MeOH/CH$_2$Cl$_2$, $R_f$ alcohol 0.25; $R_f$ mesylate 0.37). After 24 h, 4M NaOH (5 mL) was added with stirring. The organic layer was separated, dried over anhydrous $Na_2SO_4$, filtered and concentrated under reduced pressure to yield mesylate 20 (99 mg, 0.24 mmol, 80% yield).

19

$^1$H NMR ($CD_3OD$): δ 3.55 (t, 2H), 3.28 (t, 2H), 3.24 (t, 2H), 3.04 (q, 2H), 1.62-1.81 (m, 4H), 1.44 (s, 9H), 1.42 (s, 9H).[10b]

20

$^1$H NMR ($CDCl_3$): δ 4.25 (t, 2H, $J^3_{H-H}$=6.2 Hz), 3.28 (br s, 4H), 3.11 (br s, 2H), 3.02 (s, 3H), 1.99 (m, 2H), 1.67 (m, 2H), 1.56 (s, 3H), 1.47 (s, 9H), 1.44 (m, 9H)

(3-tert-Butoxycarbonylamino-propyl)-[3-(2-cyclopentadecylethylamino)-propyl]-carbamic acid tert-butyl ester 21

2-Cyclopentadecyl-ethylamine 18 (0.07 g, 0.28 mmol) was dissolved in $CH_2Cl_2$ and added to $Na_2CO_3$ (75 mL, 1.79 mmol) while stirring at rt. Di Boc Mesylate 20 (121 mg, 0.2957 mmol) was dissolved in $CH_2Cl_2$ (1 mL) and added to the solution dropwise. The reaction was stirred for 48 h and was monitored by TLC (10% MeOH/$CH_2Cl_2$, $R_f$ 0.34).

After the reaction was complete, $CH_2Cl_2$ (2 mL) was added and the solution was washed three times with aq. $Na_2CO_3$ (10% by w/v, 3 mL). The organic layer was separated, dried over anhydrous $Na_2SO_4$, filtered, and concentrated under reduced pressure to yield a crude yellow oil (248 mg). Column chromatography (10% MeOH/$CH_2Cl_2$, followed by 10% MeOH/1% $NH_4OH$, $CH_2Cl_2$) provided the crude as a clear oil (60 mg, 0.106 mmol, 38% yield) with a self-cyclized starting material 22 which was separated by running a second column (4.5% MeOH/$CH_2Cl_2$) to yield the byproduct 22 (27.3 mg, 0.0572 mmol, 21% yield) and the desired product 21 (32 mg, 0.056 mmol, 20% yield) as a yellow oil.

21

$^1$H NMR ($CDCl_3$): δ 3.31 (br s, 2H), 3.16 (br s, 2H), 3.03 (br s, 2H), 2.84 (br s, 4H), 2.06 (m, 2H), 1.65 (m, 4H), 1.40 (s, 18H), 1.36 (br s, 29H); $^{13}$C NMR: δ 46.89, 44.97, 37.80, 34.55, 32.38, 31.26, 29.69, 29.06, 28.33, 27.46, 26.76, 26.60, 26.50, 24.98, 24.25, 22.67. HRMS for $C_{33}H_{65}Cl_3N_3O_4$ (M+H) 567.4973, found 567.4975.

22

$^1$H NMR ($CDCl_3$): δ 4.25 (m, 2H), 3.30 (br s, 4H), 3.11 (s, 2H), 2.0 (m, 2H), 1.66 (m, 2H), 1.46 (s, 18H).

Bromomethyl-cyclopentadecane 23

The alcohol 15 (250 mg, 1.04 mmol) was placed under an inert atmosphere. Phosphorus tribromide (0.52 mmol, 49 µL) was added by syringe. The reaction immediately turned yellow and started bubbling and was stirred at rt for 1.5 h. Hexane (3 mL) was added and the reaction was refluxed at 69° C. for another 1.5 h. The reaction turned a brownish yellow color. The vessel was rinsed and the brown crude (0.48 g) was isolated. Column chromatography (100% n-hexane) was performed (with a 30:1 ratio of silica gel: crude) due to the large $R_f$ difference ($R_f$ 15: 0, $R_f$ 23: 0.8). Visualization of the TLC plate using phosphomolybdic acid and heat provided a convenient monitoring tool. The product 23 was isolated and concentrated under reduced pressure to yield a clear oil (0.21 g, 0.695 mmol, 67% yield). 23: $^1$H NMR ($CDCl_3$): δ 3.38 (d, 2H, $J^3_{H-H}$=6.1 Hz), 1.72 (m, 1H), 1.38 (br s, 28H); $^{13}$C NMR ($CDCl_3$): δ 40.39, 38.65, 31.17, 27.25, 26.87, 26.64, 26.53, 24.59.

Synthesis N-(2-Amino-ethyl)-N'-[2-(cyclopentadecylmethyl-amino)-ethyl]-ethane-1,2-diamine 25a The free base of 2,2-tetraamine 24b was generated using N,N'-Bis-(2-amino-ethyl)-ethane-1,2-diamine (3.00 g, 10.27 mmol, Sigma-Aldrich) with 4 equivalents of aq. NaOH (1M, 41 mmol, 41 mL). The water was removed and then dried by adding and removing benzene under reduced pressure to remove the excess water. Anhydrous $Na_2SO_4$ (8 equivalents, 82.3 mmol, 11.69 g) was added to a dried vessel with 25% MeOH/$CH_2Cl_2$ (50 mL). One equivalent of salicyclaldehyde (10.27 mmol, 1.10 mL) in MeOH (10 mL) was then added dropwise over 2 h at 0° C. while stirring. Upon addition of the reagent, the reaction immediately turned yellow. Imine formation was monitored by $^1$H NMR. After imine formation, the additional reactive centers were protected with di-tert-butyl dicarbonate (3 equiv., 30.87 mmol, 6.74 g) and stirred overnight. The reaction progress was checked by $^1$H NMR for full bocylation and additional di-tert-butyl dicarbonate was then added (0.3 equiv., 0.67g) while heating at 40° C. overnight to drive the reaction to completion. The reaction was again checked for N-bocylation and confirmed to be complete. Then $MeONH_2HCl$ (10.27 mmol, 0.8578g) was added in 1.5 mL of TEA. Note: $MeONH_2$ HCl was initially not soluble in the TEA, which was used to generate the free base. Upon addition of 25% MeOH/$CH_2Cl_2$ (5 mL) the methoxyamine easily dissolved and the TEA/MeOH/$CH_2Cl_2$ solution was then added dropwise to the stirring solution. Imine cleavage was monitored by NMR. Note: an oxime byproduct is formed via methoxyamine exchange with the imine The MeOH was then removed under reduced pressure, the residue was re-dissolved in $CH_2Cl_2$ and then washed with saturated $Na_2CO_3$ (22g/100 mL solution, 10 mL). The aqueous layer was extracted three times with $CH_2Cl_2$ and then the organic layer was concentrated under reduced pressure to yield a yellow oil (3.65 g). The product was separated from the crude by column chromatography (1% $NH_4OH$/10% MeOH/$CH_2Cl_2$, Product $R_f$ 25a: 0.65). The product 25a eluted as a light yellow solid (1.48 g, 3.31 mmol, 32% yield). 25a: $C_{21}H_{42}N_4O_6$ $^1$H NMR ($CDCl_3$): δ 3.31 (br s, 10H), 2.84 (br s, 2H), 1.79 (br s, 2H), 1.46 (br s, 27H); $^{13}$C NMR ($CDCl_3$): δ 155.52, 76.59, 46.24, 45.45, 40.24, 39.08, 28.06; HRMS for $C_{21}H_{42}N_4O_6$ (M+H) Theory 446.3121, Found 446.3104; Anal $C_{21}H_{42}N_4O_6$·0.2 $H_2O$ Theory: C, 56.03, H, 9.49, N, 12.45 Found: C, 55.87, H, 9.39, N, 12.23.

N-[2-(2-Amino-ethylamino)-ethyl]-N'-(2-cyclopentadecylamino-ethyl)-ethane-1,2-diamine 25b The free base of tetraethylenepentamine pentahydrochloride 24c (N-(2-Amino-ethyl)-N'-[2-(2-amino-ethylamino)-ethyl]-ethane-1,2-diamine, Sigma Aldrich) (3 g, 8.07 mmol) was generated with 5 equivalents of NaOH (40.4 mmol, 1.61 g, 40.35 mL). The water was then removed by addition of benzene as an azeotrope and then removal of benzene under reduced pressure. Anhydrous sodium sulfate was added (64.6 mmol, 9.18 g) and 25% MeOH/DCM added as solvent (30 mL). After the generation of the free base, one equivalent of salicylaldehyde was added (8.07 mmol, 1.160 g/mL, 850 µL) to protect the terminal amine and the solution immediately turned bright yellow. After protection was complete by NMR, the remaining amines were protected with di-tert-butyl dicarbonate (4 equivalents, 7.05 g, 32.29 mmol) and the reaction was heated at 40° C. overnight. After complete bocylation was verified by NMR, the imine was cleaved with 1 equivalent of methoxyamine (8.07 mmol, 0.674 g, in 1.13 mL of TEA and 5 mL of MeOH/CH$_2$Cl$_2$) and the disappearance of the imine peak at 8.34 ppm by $^1$H NMR. After conversion to the free amine was complete, the solvent (MeOH) was removed and residue was redissolved in DCM and then washed with saturated aq. Na$_2$CO$_3$ (30 mL) to generate the free base. The organic layer was separated, dried over anhydrous sodium sulfate, filtered and concentrated to give a red brown solid (6.24 g). The crude solid was separated by column chromatography (1% NH$_4$OH/10% MeOH/CH$_2$Cl$_2$, product R$_f$ 25b: 0.5) to generate a light red solid (1.23 g, 2.09 mmol, 26% yield). 25b: $^1$H NMR (CDCl$_3$): δ 3.32 (br s, 14H), 2.86 (br s, 2H), 1.89 (br s, 2H), 1.46 (s, 36H).; $^{13}$C NMR (CDCl$_3$): δ 156.12, 80.1, 50.12, 47.32, 45.72, 40.82, 39.40, 28.4; Anal C$_{28}$H$_{55}$N$_5$O$_8$ Theory: C, 57.02, H, 9.40, N, 11.87 Found: C, 56.75, H, 9.31, N, 11.61; HRMS for C$_{28}$H$_{55}$N$_5$O$_8$ (M+H) Theory 589.4079, Found 589.4051.

(2-tert-Butoxycarbonylamino-ethyl)-[2-(tert-butoxy-carbonyl-cyclopentadecylmethyl-amino)-ethyl]-carbamic acid tert-butyl ester 27a Triamine 24a (N1-(2-Amino-ethyl)-ethane-1,2-diamine, Sigma, 255 mg, 2.47 mmol) was added to bromide 23 (250 mg, 0.82 mmol) dropwise in CH$_3$CN (3 mL) along with K$_2$CO$_3$ (1.17 g, 8.47 mmol) at 120° C. After 48 h, $^1$H NMR showed complete disappearance of starting material and the reaction was concentrated and ressuspended in DCM and washed with 0.1M NaOH. The organic layer was separated, dried over anhydrous Na$_2$SO$_4$, filtered and concentrated to give a light yellow oil (272 mg). Di-tert-butyl dicarbonate was added (540 mg, 2.47 mmol) in 25% MeOH/DCM (10 mL) at 40° C. and the reaction stirred overnight. Bocylation was assessed by NMR and when complete the reaction was concentrated and redissolved in DCM and washed with aq. Na$_2$CO$_3$. The organic layer was separated, dried over anhydrous sodium sulfate, filtered and concentrated under reduced pressure to give a yellow oil (706 mg). The crude was then purified by column chromatography (2% MeOH/DCM R$_f$ 27a: 0.4) to give 27a as a viscous yellow oil (154 mg, 25% yield). 27a: $^1$H NMR (CDCl$_3$): δ 3.30 (m, 8H), 3.06 (m, 2H), 3.04 (m, 1H), 1.68 (s, 1H), 1.45 (s, 27H), 1.31 (br s, 28H). $^{13}$C NMR (CDCl$_3$): δ. 155.85, 79.89, 52.46, 46.72, 45.50, 39.78, 36.20, 30.17, 28.42, 26.76, 24.43; HRMS for C$_{35}$H$_{67}$N$_3$O$_6$ (M+H): theory 625.5043; found 625.5030; Anal Calcd for C$_{35}$H$_{67}$N$_3$O$_6$: theory C, 67.16, H, 10.79; N, 6.71; found C, 67.42, H, 10.92, N, 6.63.

[2-(tert-Butoxycarbonyl-{2-[tert-butoxycarbonyl-(2-tert-butoxycarbonylamino-ethyl)-amino]-ethyl}-amino)-ethyl]-cyclopentadecylmethyl-carbamic acid tert-butyl ester 27b Triethylene tetra-amine tetra HCl (N,N'-Bis-(2-amino-ethyl)-ethane-1,2-diamine, Sigma) (1.0 g, 3.42 mmol) was dissolved in 1M NaOH (13.8 mL) to give the free tetraamine base 24b. The aqueous layer was then removed and chased with benzene for complete water removal to give dry 24b plus NaCl. Mesylate 16 (628 mg, 2 mmol) was dissolved in CH$_3$CN with K$_2$CO$_3$ (391 mg: 2.83 mmol), the reaction showed complete conversion after 72 h at 50° C. by $^1$H NMR. The reaction was concentrated to provide a residue, which was dissolved in DCM and washed with 0.1M NaOH (30 mL). A difficult emulsion ensued. The organic layer was separated, dried over anhydrous Na$_2$SO$_4$, filtered and concentrated to give organic layer #1. The remaining emulsion/aqueous layer was concentrated and re-dissolved in DCM at a lower temperature and any remaining precipitates were filtered off. The precipitates were washed with DCM and the organic filtrate was pooled with organic layer #1 and concentrated to give a yellow viscous oil (806 mg). The crude oil was re-dissolved in 25% MeOH/DCM and reacted with di-tert-butyl dicarbonate (8.75 mmol, 1.91 g). The reaction was monitored for bocylation by NMR and then worked up in saturated aq. Na$_2$CO$_3$ and DCM. The organic layer was separated, dried over anhydrous Na$_2$SO$_4$, filtered and concentrated to give a yellow oil (1.57 g). Column chromatography (25% EtOAc/hexanes, R$_f$ 27b: 0.39) gave 27b as a viscous oil (383 mg, 0.5 mmol, 25% yield).

27b $^1$H NMR (CDCl$_3$): δ 3.32 (m, 12H), 3.08 (br s, 1H), 3.03 (br s, 2H), 1.46 (s, 36H), 1.33 (br s, 29H); $^{13}$C NMR (CDCl$_3$): δ 155.4, 80.16, 79.41, 51.68, 45.41, 36.13, 35.78, 36.13, 35.78, 30.18, 28.45, 26.77, 26.38, 24.44; HRMS C$_{42}$H$_{80}$N$_4$O$_8$ (M+H) Theory: 768.5987, Found: 768.5976; Anal Calcd C$_{42}$H$_{80}$N$_4$O$_8$ Theory: C, 65.59, H, 10.48, N, 7.28 Found: C, 65.89, H, 10.64, N, 7.26.

[2-(Cyclopentadecylmethyl-amino)-ethyl]-carbamic acid tert-butyl ester 27c

The commercially-available mono N-Boc diamine 28 ((2-Amino-ethyl)-carbamic acid tert-butyl ester, Sigma, 286 mg, 1.78 mmol) was added to mesylate 16 (508 mg, 1.59 mmol) in CH$_3$CN (20 mL) with K$_2$CO$_3$ (0.72 g) at 50° C. After 5 days the reaction showed 50% conversion, most of the CH$_3$CN was stripped off (leaving 5 mL) and heated overnight for complete conversion. The solvent was removed under reduced pressure, re-dissolved in DCM and washed with water. The crude (620 mg) was then purified by column chromatography (7% MeOH/DCM Rf 27c: 0.4) to give 27c as a clear oil (75 mg, 0.196 mmol, 12% yield) as well as a large amount of what appeared to be a cyclized urea byproduct 27d (250 mg) 27c: $^1$H NMR (CD$_4$O): δ 3.23 (broad s, 2H), 2.78 (br s, 2H), 2.60 (br s, 2H), 1.63 (s, 1H), 1.45 (s, 9H), 1.37 (br s, 28H); $^{13}$C NMR (CD$_4$O): δ 150.80, 68.01, 50.44, 31.87, 28.88, 28.22, 28.03, 27.91, 27.75; HRMS for C$_{23}$H$_{46}$N$_2$O$_2$ (M+H) Theory: 382.3558 Found: 382.3559; Anal Calcd for C$_{23}$H$_{46}$N$_2$O$_2$ 0.3 H$_2$O: theory C, 71.19, H, 12.10, N, 7.22; found C, 71.02, H, 12.05, N, 7.20.

References

[1] WHO report: antimicrobial resistance: global report on surveillance 2014. http://www.who.int/drugresistance/documents/surveillancereport/en/
[2] F. Prabhavathi *Nat. Biotechnol.* 2006, 24, 1497-1503.
[3] A. E. Pop-Vicas, E. M. D'Agata, *Clin. Infect. Dis.* 2005, 40, 1792-1798.
[4] J. M. Coelho, J. F. Turton, M. Kaufmann, J. Glover, N. Woodford, M. Warner, M. F. Palepou, T. L., B. C. Patel, D. M. Livermore, *J. Clin. Microbiol.* 2006, 44, 3623-3627.
[5] M. C. Jennings, K. P. C. Minbiole, W. M. Wuest, *ACS Infect. Dis.,* 2015, 1, 288-303.

[6] C. Y. Wang, J. S. Jerng, K. Y. Chen, L. N. Lee, C. J. Yu, P. R. Hsueh, P. C. Yang, *Clin. Microbiol. Infect.* 2006, 12, 63-68.
[7] S. D. Mentzelopoulos, M. Pratikaki, E. Platsouka, H. Kraniotaki, D. Zervakis, A. Koutsoukou, S. Nanas, O. Paniara, C. Roussos, E. Giamarellos-Bourboulis, C. Routsi, S. G. Zakynthinos, *Intensive Care Med.* 2007, 33, 1524-1532.
[8] A. Antoniadou, F. Kontopidou, G. Poulakou, E. Koratzanis, I. Galani, E. Papadomichelakis, P. Kopterides, M. Souli, A. Armaganidis, H. Giamarellou, *J. Antimicrob. Chemother.* 2007, 59, 786-790.
[9] M. E. Falagas, S. K. Kasiakou, *Clin. Infect. Dis.* 2005, 40, 1333-1341.
[10] S. Biswas, J. M. Brunel, J. C. Dubus, M. Reynaud-Gaubert, J. M. Rolain, *Expert Rev. Anti Infect. Ther.* 2012, 10, 917-934.
[11] H. Labischinski, G. Barnickel, H. Bradaczek, D. Naumann, E. T. Rietschel, P. Giesbrecht, *J. Bacteriol.* 1985, 162, 9-20.
[12] M. Vaara, *Microbiol. Rev.* 1992, 56, 395-411.
[13] H. Nikaido, Outer Membrane. In: Neidhardt F C, Curtis III R, Ingraham J L, eds. *Escherichia coli* and *Salmonella*: Cellular and Molecular Biology. Washington: ASM press. 1996, 29-47.
[14] R. Hancock, *Trends Microbiol.* 1997, 5, 37-42.
[15] T. Murata, W. Tseng, T. Guina, S. I. Miller, H. Nikaido, *J. Bacteriol.* 2007, 189, 7213-7222.
[16] M. Vaara, *Antimicrob. Agents Chemother.* 1993, 37, 354-356.
[17] H. Nikaido, *Microbiol. Mol. Biol. Rev.* 2003, 67, 593-656.
[18] M. Zasloff, *Nature* 2002, 415, 389-395.
[19] L. Djouhri-Bouktab, J. M. Rolain, J. M. Brunel, *Anti-infective Agents* 2014, 12, 95-103.
[20] M. Blanchet, D. Borselli, J. M. Brunel, *Future Med. Chem.* 2016, 8, 963-973.
[21] C. Pieri, D. Borselli, C. Di Giorgio, M. De Meo, J. M. Bolla, N. Vidal, S. Combes, J. M. Brunel, *J. Med. Chem.* 2014, 57, 4263-4272.
[22] J. M. Brunel, A. Lieutaud, V. Lome, J. M. Pagès, J. M. Bolla, *Bioorg. Med. Chem.* 2013, 21, 1174-1179.
[23] D. E. Williams, P. Lassota, R. J. Andersen, *J. Org. Chem.* 1998, 63, 4838-4841.
[24] A. Muth, V. Pandey, N. Kaur, M. Wason, C. Baker, X. Han, T. R. Johnson, D. A. Altomare, O. Phanstiel IV, *J. Med. Chem.* 2014, 57, 4023-4034.
[25] A. Muth, M. Madan, J. J. Archer, N. Ocampo, L. Rodriguez, O. Phanstiel IV, *J. Med. Chem.* 2014, 57, 348-363.
[26] K. Alhanout, S. Malesinki, N. Vidal, V. Peyrot, J. M. Rolain, J. M. Brunel, *J. Antimicrob. Chemother.* 2010, 65, 1688-1693.
[27] T. Wieder, P. J. Sims, *J. Membr. Biol.* 1985, 84, 249-258.
[28] O. Lomovskaya, M. S. Warren, A. Lee, J. Galazzo, R. Fronko, M. Lee, J. Blais, D. Cho, S. Chamberland, T. Renau, R. Leger, S. Hecker, W. Watkins, K. Hoshino, H. Ishida, V. J. Lee, *Antimicrob. Agents Chemother.* 2001, 45, 105-116.
[29] Y. Matsumoto, K. Hayama, S. Sakakihara, K. Nishino, H. Noji, R. Iino, A. Yamaguchi, *PLoS One* 2011, 6, e18547.
[30] M. Mallea, J. Chevalier, C. Bornet, A. Eyraud, A. Davin-Regli, C. Bollet, J.-M. *Pagès, Microbiology* 1998, 144, 3003-3009.
[31] M. Wu, R. E. W. Hancock, *J. Biol. Chem.* 1999, 274, 29-35.
[32] L. Amaral, A. Martins, G. Spengler, J. Molnar, *Front. Pharmacol.* 2013, 4, 168.
[33] J. A. Bohnert, S. Schuster, M. Szymaniak-Vits, W. V. Kern, *PLoS One* 2011, 6, e21196.
[34] A. Mariscal, R. M. Lopez-Gigosos, M. Carnero-Varo, J. Fernandez-Crehuet, *Appl. Microbiol. Biotechnol.* 2009, 82, 773-783.
[35] B. Wang, B. Pachaiyappan, J. D. Gruber, M. G. Schmidt, Y.-M. Zhang, P. M. Woster, *J. Med. Chem.* 2016, 59, 3140-3151.
[36] Members of the SFM Antibiogram Committee, *Int. J. Antimicrob. Agents* 2003, 21, 364-391.
[37] N. Kaur, J.-G. Delcros, B. Martin, O. Phanstiel IV, *J. Med. Chem.* 2005, 48, 3832-3839.
[38] C. Wang, J.-G. Delcros, J. Biggerstaff, O. Phanstiel IV, *J. Med. Chem.* 2003, 46, 2663-2671.
[39] C. Wang, J.-G. Delcros, J. Biggerstaff, O. Phanstiel IV, *J. Med. Chem.* 2003, 46, 2672-2682.
[40] C. Wang, J.-G. Delcros, L. Cannon, F. Konate, H. Carias, J. Biggerstaff, R. A. Gardner, O. Phanstiel IV, *J. Med. Chem.* 2003, 46, 5129-5138.
[41] O. Phanstiel IV, N. Kaur, J.-G. Delcros, *Amino Acids* 2007, 33, 305-313.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The full disclosure of cited references are incorporated herein in their entirety to the extent not inconsistent with the teachings herein.

The invention claimed is:

1. A method of treating a microbe infection in a subject in need of treatment, comprising administering an effective amount of one or more compounds of the following formula:

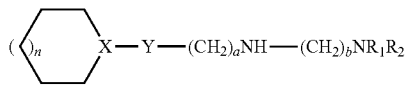

where n=10-13; X=CH; Y=CH$_2$ or N; a=2-8; b=0-8; R$_1$=H or alkyl or alkylamino or alkyl-N-alkylamino or alkylpolyamino; alkylalcohol or alkyl-O-alkylamino or polyether; alkylamide and R2=H or Me; or a pharmaceutically acceptable salt thereof;

16a

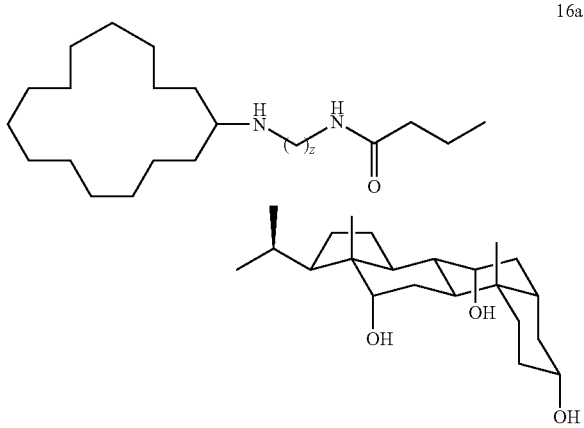

41
-continued

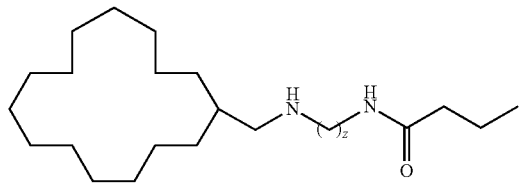
16b

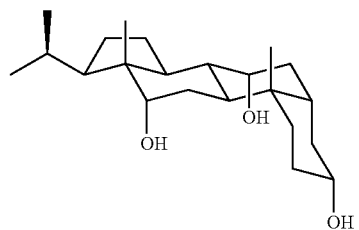

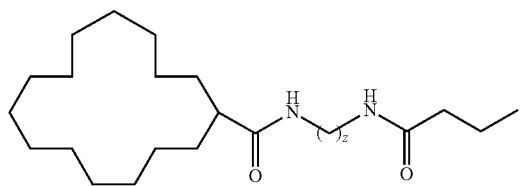
16c

42
-continued

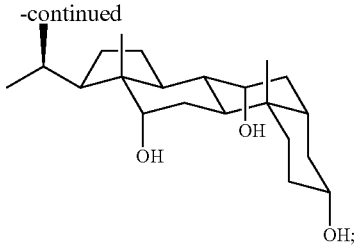

wherein z = 2-16 or a pharmaceutically acceptable salt thereof;
and optionally co-administering an antibiotic.

2. The method of claim 1, wherein the antibiotic is selected from the group consisting of amoxicillin, doxycycline, erythromycin, chloramphenicol, cephalexin, ciprofloxacin, clindamycin, methicillin, metronidazole, penicillin, rifampicin, azithromycin, sulfamethoxazole/trimethoprim, amoxicillin/clavulanate, levofloxacin, and vancomycin.

3. The method of claim 1, wherein the antibiotic is selected from the group consisting of ampicillin, vancomycin, gentamicin, tetracycline, chloramphenicol, rifampin, norfloxacin, rifaximin, tigecycline, furazolidone, triclosan, cefoperazone, silver sulfadiazine, dapsone, gemifloxacin, sulfadimidine, enoxacin, sulfisoxazole, ceftolozane, prontosil, sulfapyridine, sulfamerazine, grepafloxacin, sulfamethoxypyridazine, sulfalene, acetic acid/hydrocortisone, sulfaphenazole, sulfametoxydiazine, sulfamoxole, sulfabenzamide, sulfametrole, viridicatumtoxin B, sulfametomidine, sulfaperin, and sulfathiourea.

4. The method of claim 1, wherein the antibiotic is effective at a lower dosage in combination with the one or more compounds than without the one or more compounds.

* * * * *